(12) United States Patent
Herbert et al.

(10) Patent No.: US 9,273,090 B1
(45) Date of Patent: Mar. 1, 2016

(54) HETEROLOGOUS EXPRESSION OF CELLULAR ADHESION MOLECULES

(75) Inventors: Stephen K. Herbert, Laramie, WY (US); Levi G. Lowder, Laramie, WY (US)

(73) Assignee: University of Wyoming, Laramie, WY (US)

( * ) Notice: Subject to any disclaimer, the term of this patent is extended or adjusted under 35 U.S.C. 154(b) by 203 days.

(21) Appl. No.: 13/408,722

(22) Filed: Feb. 29, 2012

Related U.S. Application Data

(60) Provisional application No. 61/448,135, filed on Mar. 1, 2011.

(51) Int. Cl.
*C12N 1/13* (2006.01)
*C07K 4/08* (2006.01)

(52) U.S. Cl.
CPC ........................................ *C07K 4/08* (2013.01)

(58) Field of Classification Search
None
See application file for complete search history.

(56) References Cited

U.S. PATENT DOCUMENTS

| | | | |
|---|---|---|---|
| 2010/0184180 A1* | 7/2010 | Surzycki et al. | 435/168 |
| 2010/0279390 A1 | 11/2010 | Saphire | |
| 2011/0159595 A1 | 6/2011 | Mendez et al. | |
| 2012/0288918 A1* | 11/2012 | Hopkins et al. | 435/257.2 |

FOREIGN PATENT DOCUMENTS

| WO | WO2009158658 | 12/2009 |
|---|---|---|

OTHER PUBLICATIONS

Huber et al. EMBO J. 13, 18, 4212-4222, 1994.*
Schroda et al, Plant J., 21, 2, 121-131, 2000.*
Sizova et al. (Gene, 277:221-229, 2001.*
Croft et al., Proc. Natl. Sci. USA, 204, 52, 20770-20775, 2007.*
Fuhrmann et la., Plant J., 19(3):353-361, 1999.*
Franklin et al., Curr. Opinion Plant Biol., 7:159-165, 2004.*
Lowder et al. Harvesting Algae: Engineering Auto-Flocculation in Chalmydomonas Reinhardtii (abstract), 20th Western Photosynthesis Conference, Jan. 6-9, 2011, p. 18.
Feng et al. Dunaliella salina as a novel host for the production of recombinant proteins. Appl Microbiol Biotechnol (2014) 98:4293-4300.
Sun et al. Expression of Foreign Genes in Dunaliellaby Electroporation. Molecular Biotechnology. (2005) 30:185-192.
Schirrmeister et al. The origin of multicellularity in cyanobacteria. BMC Evolutionary Biology (2011) 11:45.
Catt et al. Cell Wall Glycoproteins from Chlamydomonas reinhardii, and their Self-Assembly. Planta. (1978) 138:91-98.
Lurling et al. Palmelloids formation in Chlamydomonas reinhardtii: defense against rotifer predators? Ann. Limnol.—Int. J. Lim. (2006) 42:65-72.
Hallmann, Armin. The pherophorins: common, versatile building blocks in the evolution of extracellular matrix architecture in Volvocales. The Plant Journal. (2006) 45:292-307.
U.S. Appl. No. 13/772,635. Office Action dated Mar. 31, 2015.

* cited by examiner

*Primary Examiner* — Nancy T Vogel
(74) *Attorney, Agent, or Firm* — James M. Weatherly; Cochran Freund & Young LLC

(57) ABSTRACT

Methods for the production of unicellular photosynthetic organisms capable of producing cell adhesion proteins are disclosed. DNA constructs as well as methods for integration of the DNA constructs into the genomes of unicellular photosynthetic organisms for the expression of cell adhesion proteins are also disclosed.

8 Claims, 15 Drawing Sheets

HETEROLOGOUS EXPRESSION OF CELLULAR ADHESION MOLECULES

CROSS REFERENCE TO RELATED APPLICATIONS

This application is a non-provisional patent application of and claims the benefit of U.S. Provisional Application No. 61/448,135 filed Mar. 1, 2011, the entire contents of which are incorporated herein by reference for all purposes.

ACKNOWLEDGEMENT OF FEDERAL RESEARCH SUPPORT

This invention was made, in part, with government support awarded by the National Aeronautics and Space Agency, grant # NNG05165H, and by the United States Department of Agriculture, grant #2006-35318-17445. Accordingly, the United States government has certain rights in this invention.

SUBMISSION OF SEQUENCE LISTING

The Sequence Listing associated with this application is filed in electronic format via EFS-Web and is hereby incorporated by reference into the specification in its entirety. The name of the text file containing the Sequence Listing is UOWY24USU1sequencefinal.txt.

BACKGROUND

All publications cited in this application are herein incorporated by reference.

Photosynthetic unicells, such as *Chlamydomonas reinhardtii*, produce complex and diverse organic compounds from carbon dioxide, inorganic salts, and water by means of photosynthesis. However, unicells are single cells that do not physically attach to other cells under most circumstances.

Multicellular photosynthetic organisms, such as *Volvox carteri*, have cell walls, also known as extracellular matrices that bind photosynthetic cells together in multicellular photosynthetic organisms. Examples of cell walls include, but are not limited to, the lignified, cellulosic cell walls of plants, the glycoprotein extracellular matrices of many green algae, the siliceous cell walls of diatoms, and the calcareous cell walls of coccolithophorids and coralline red algae. All cell walls have a certain chemical composition that determines their physical properties. The chemical composition of cell walls is determined, in turn, by the specific organic and inorganic molecules secreted from the cells during biological development and by the order in which the various molecules are secreted.

*Volvox carteri* is a multicellular green alga that exhibits cell-cell adhesion during embryonic development. The adhesion of cells in *V. carteri* is primarily mediated by glycoproteins, examples of which are designated Algal-CAM, ISG, V1 and V2. These cell adhesion molecules are proteins located on the cell surface involved with the binding with other cells or with the extracellular matrix of the cell. Cell adhesion molecules help cells bind to each other.

SUMMARY

An embodiment of the present invention may comprise a DNA construct, wherein the DNA construct comprises a promoter operably linked to a cell adhesion protein coding sequence.

An embodiment of the present invention may further comprise a transgenic unicellular photosynthetic organism having a DNA construct stably integrated into the unicellular photosynthetic organism's genome under conditions suitable for expression of the DNA construct in an extracellular matrix of the unicellular photosynthetic organism, wherein the DNA construct expresses a protein in the extracellular matrix of the unicellular photosynthetic organism, and wherein the expressed protein is a cell adhesion protein.

An embodiment of the present invention may further comprise a method for producing a transgenic unicellular photosynthetic organism which comprises growing a transgenic unicellular photosynthetic organism having a DNA construct stably integrated into a genome under conditions suitable for an expression of the DNA construct in the transgenic unicellular photosynthetic organism, wherein the DNA construct expresses a protein in the extracellular matrix of the unicellular photosynthetic organism, and wherein the expressed protein is a cell adhesion protein.

BRIEF DESCRIPTION OF THE SEQUENCE LISTINGS

Figure 1:
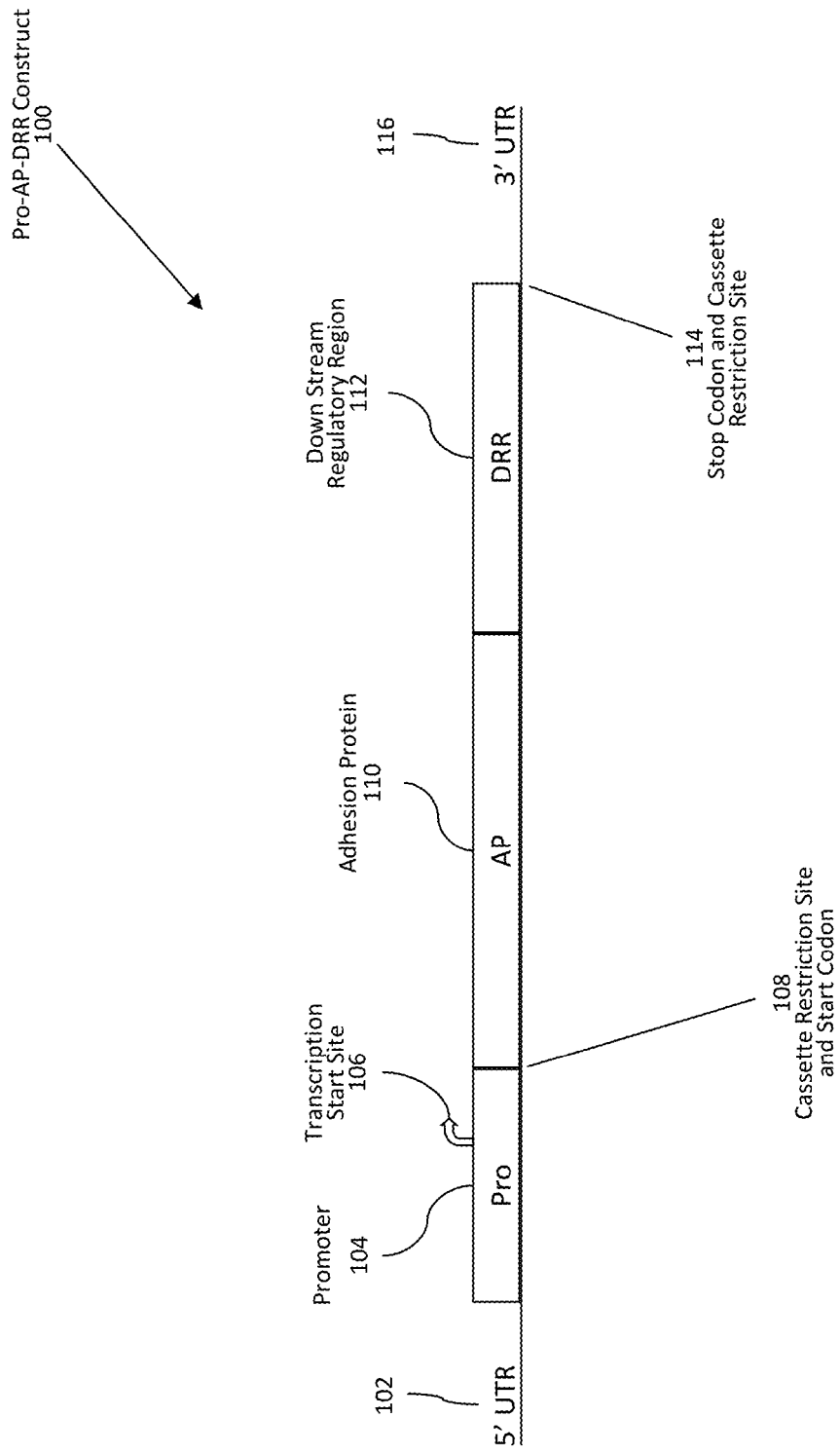
FIG. 1 is a map of a DNA construct, represented as Pro-AP-DRR that includes (from 5' to 3'), promoter, cell adhesion protein coding sequence and a downstream regulatory region.

SEQ ID NO:1 discloses the nucleic acid sequence for the Algal-CAM signal peptide and adhesion protein transgene (GENBANK Accession No.: X80416).

SEQ ID NO:2 discloses the protein sequence for the Algal-CAM signal peptide and adhesion protein transgene (GENBANK Accession No.: X80416).

SEQ ID NO:3 discloses the nucleic acid sequence of the *Volvox* V1 transgene base pairs 10 to 1782 (GENBANK Accession No.: XM_002956879).

SEQ ID NO:4 discloses the protein sequence of the *Volvox* V1 transgene (GENBANK Accession No.: XP_002956925).

SEQ ID NO:5 discloses the nucleic acid sequence of the *Volvox* V2 transgene base pairs 21-1049 (GENBANK Accession No.: XM_002958810).

SEQ ID NO:6 discloses the protein sequence of the *Volvox* V2 transgene (GENBANK Accession No.: XP_002958856).

SEQ ID NO:7 discloses the nucleic acid sequence of the *Volvox* ISG transgene (GENBANK Accession No.: XM_002949857).

SEQ ID NO:8 discloses the protein sequence of the *Volvox* ISG transgene (GENBANK Accession No.: XP_002949903).

SEQ ID NO:9 discloses the nucleic acid sequence for the RbcS2 promoter flanked by enhancer elements of Hsp70A and RbcS2 intron 1 ("Hsp70A/RbcS2").

SEQ ID NO:10 discloses the nucleic acid sequence for the PSAD promoter.

SEQ ID NO:11 discloses the nucleic acid sequence for the paromomycin resistance marker (GENBANK Accession No.: AF182845.2).

SEQ ID NO:12 discloses the nucleic acid sequence for the paromomycin resistance marker (aph VIIIsr) w/ upstream Hsp70A/RbcS2 promoter and intron 1.

SEQ ID NO:13 discloses the nucleic acid sequence for the THI4 riboswitch alt. spliced exon with 5' NotI and 3' NdeI.

SEQ ID NO:14 discloses the nucleic acid sequence for the complete plasmid with Hsp70/RbcS2 promoter and intron 1 promoter, Algal-CAM protein and fluorescent protein plasmid pSI105.

SEQ ID NO:15 discloses the nucleic acid sequence for the oligonucleotide ACAMCDS2fwd.

SEQ ID NO:16 discloses the nucleic acid sequence for the oligonucleotide ACAMCDS2rev.

SEQ ID NO:17 discloses the nucleic acid sequence for the forward primer FwdxhoIBglII.

SEQ ID NO:18 discloses the nucleic acid sequence for the reverse primer RevBamHI.

SEQ ID NO:19 discloses the nucleic acid sequence for the forward primer Fwdw/BglII.

SEQ ID NO:20 discloses the nucleic acid sequence for the reverse primer Revw/MscI.

SEQ ID NO:21 discloses the nucleic acid sequence for the reverse primer Revw/MscI with linker.

SEQ ID NO:22 discloses the nucleic acid sequence for the PCR forward primer Scnfwd1.

SEQ ID NO:23 discloses the nucleic acid sequence for the PCR reverse primer Scnrev1.

SEQ ID NO:24 discloses the nucleic acid sequence for the forward primer ScnRTPCRfwd2.

SEQ ID NO:25 discloses the nucleic acid sequence for the reverse primer ScnRTPCRrev2.

SEQ ID NO:26 discloses the nucleic acid sequence for the forward primer cActinfwd1 directed toward cActin mRNA.

SEQ ID NO:27 discloses the nucleic acid sequence for the reverse primer cActinrev1 directed toward cActin mRNA.

DETAILED DESCRIPTION OF THE EMBODIMENTS

Embodiments of the present invention include DNA constructs as well as methods for integration of the DNA constructs into photosynthetic unicellular organisms for the expression of cell adhesion molecules, other cell wall, outer membrane or extracellular matrix proteins that govern production and secretion of cell wall, outer membrane extracellular matrix materials by the cellular endomembrane system, or proteins associated with the plasma membrane that contribute to the shape or composition of the cell wall, outer membrane or extracellular matrix. A "construct" is an artificially constructed segment of DNA that may be introduced into a target unicellular photosynthetic organism.

As used herein, the term "expression" includes the process by which information from a gene is used in the synthesis of a functional gene product, such as the expression of cell adhesion proteins in the cell wall, outer membrane or extracellular matrix of unicellular photosynthetic organisms. These products are often proteins, but in non-protein coding genes such as rRNA genes or tRNA genes, the product is a functional RNA. The process of gene expression is used by all known life, i.e., eukaryotes (including multicellular organisms), prokaryotes (bacteria and archaea), and viruses, to generate the macromolecular machinery for life. Several steps in the gene expression process may be modulated, including the transcription, up-regulation, RNA splicing, translation, and post-translational modification of a protein.

As shown in FIG. 1, a construct is generally represented as Pro-AP-DRR 100, where starting at the 5' UTR 102 a promoter such as the PSAD promoter (SEQ ID NO: 10) is provided as Pro 104 with a transcription start site 106. AP 110 is a cell adhesion protein such as the Algal-CAM (SEQ ID NO:2), V1 (SEQ ID NO:4), V2 (SEQ ID NO:6), ISG (SEQ ID NO:8), cadherin or claudin proteins with a restriction site and start codon 108 on the 5' end of the cell adhesion protein. A downstream regulatory region 112 includes the transcription terminator sequence as well as the stop codon and 3' cassette restriction site 114 on the 3'UTR 116. The downstream regulatory region may include a peptide tag such as the FLAG 3x tag. Each of these components is operably linked to the next, i.e., the promoter is operably linked to the 5' end of the adhesion protein sequence encoding the cell adhesion protein, the cell adhesion protein coding sequence is operably linked to the 5' end of the downstream regulatory region. The DNA construct Pro-AP-DRR is then integrated into a unicellular photosynthetic organism such as *Chlamydomonas reinhardtii* and organisms expressing the cell adhesion protein, including expression in the cell wall or extracellular matrix of the organism, are then generated including but not limited to cyanobacteria including but not limited to *Arthrospira* spp., *Spirulina* spp., *Synechococcus elongatus* 7942, *Synechococcus* spp., *Synechosystis* spp. PCC 6803, *Synechosystis* spp., and *Spirulina plantensis*, *H. salinarum*, *Calothrix* spp., *Anabaena flos-aquae*, *Aphanizomenon* spp., *Anadaena* spp., *Gleotrichia* spp., *Oscillatoria* spp. and *Nostoc* spp.; eukaryotic unicellular algae such as but not limited to *Chaetoceros* spp., *Chlamydomonas reinhardii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantscia* spp., *Hematococcus* spp., *Isochrysis* spp., *Laminaria* spp., *Nannochloropsis* spp., *Navicula* spp., *Pleurochrysis* spp. and *Sargassum* spp.

As used herein "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

Figure 2:
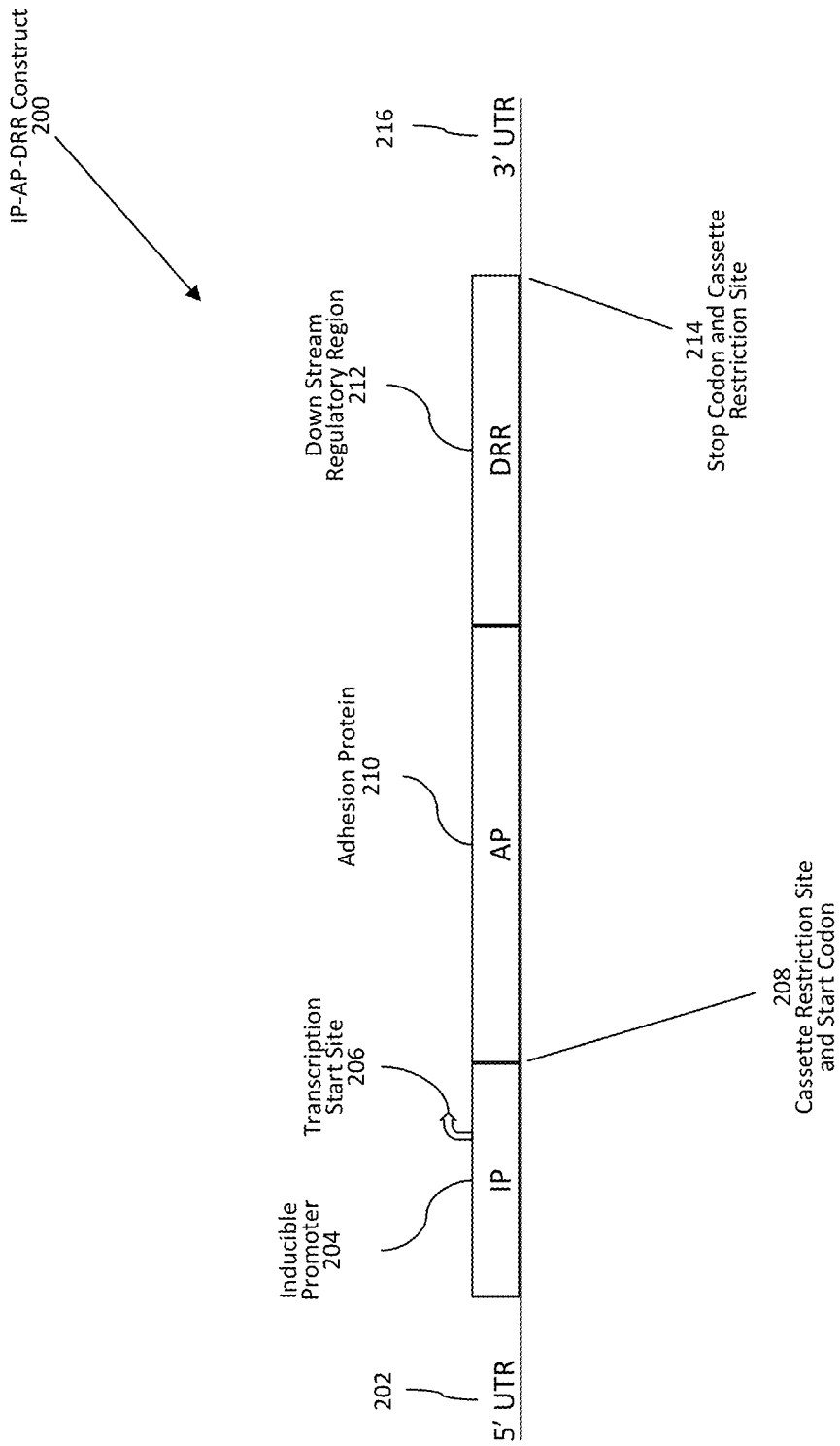
FIG. 2 is a map of a DNA construct, represented as IP-AP-DRR that includes (from 5' to 3'), an inducible promoter, a cell adhesion protein coding sequence and a downstream regulatory region.

As shown in FIG. 2, a construct is generally represented as IP-AP-DRR 200, where starting at the 5' UTR 202 an inducible promoter such as the PSAD promoter is provided as IP 204 with a transcription start site 206. AP 210 is a cell adhesion protein such as the Algal-CAM (SEQ ID NO:2), V1 (SEQ ID NO:4), V2 (SEQ ID NO:6), ISG (SEQ ID NO:8), cadherin or claudin proteins with a restriction site and start codon 208 on the 5' end of the adhesion protein. A downstream regulatory region 212 includes the transcription terminator sequence as well as the stop codon and 3' cassette restriction site 214 on the 3'UTR 216. The downstream regulatory region may include a peptide tag such as the FLAG 3x tag. Each of these components is operably linked to the next, i.e., the promoter is operably linked to the 5' end of the adhesion protein sequence encoding the cell adhesion protein, the cell adhesion protein coding sequence is operably linked to the 5' end of the downstream regulatory region. The DNA construct IP-AP-DRR is then integrated into a unicellular photosynthetic organism such as *Chlamydomonas reinhardtii* and organisms expressing the cell adhesion protein, including expression in the cell wall or extracellular matrix of the organism, are then generated.

Figure 3:
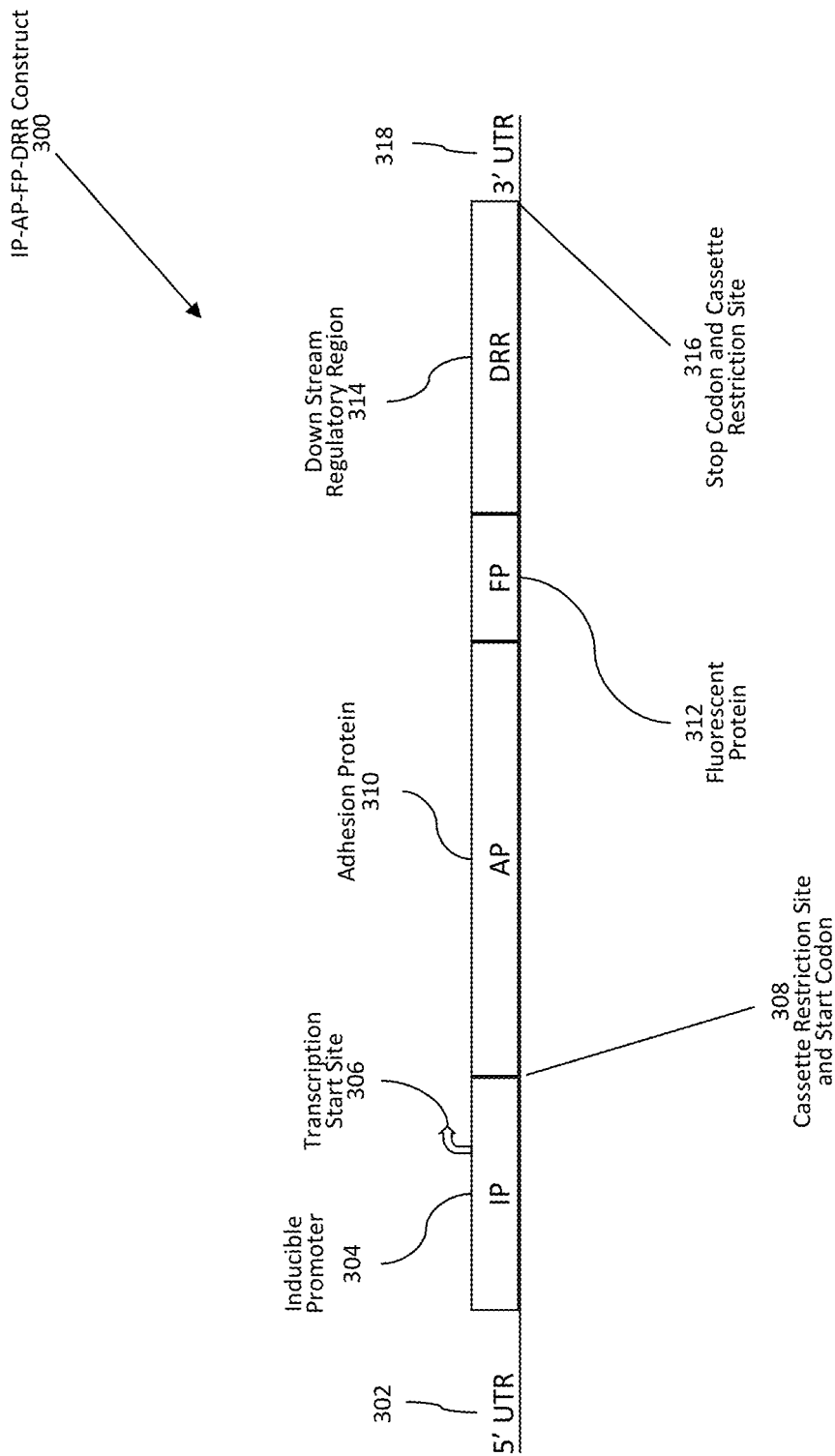
FIG. 3 is a map of a DNA construct, represented as IP-AP-FP-DRR that includes (from 5' to 3'), an inducible promoter, a cell adhesion protein coding sequence, a fluorescent protein fusion coding sequence and a downstream regulatory region.

As shown in FIG. 3, a construct is generally represented as IP-AP-FP-DRR 300, where starting at the 5' UTR 302 an inducible promoter such as the RBCS2 promoter flanked by enhancer elements of HSP70A and RBCS2 intron 1 (SEQ ID NO: 9) is provided as IP 304 with a transcription start site 306. AP 310 is a cell adhesion protein such as the Algal-CAM (SEQ ID NO:2), V1 (SEQ ID NO:4), V2 (SEQ ID NO:6), ISG (SEQ ID NO:8), cadherin or claudin proteins with a restriction site and start codon 308 on the 5' end of the adhesion protein. FP, 312 is a fluorescent fusion protein such as a yellow fluorescent protein (YFP), a cyan fluorescent protein (CFP), a red fluorescent protein (mRFP). The downstream regulatory region DRR 314 includes the transcription terminator sequence as well as the stop codon and 3' cassette restriction site 316 on the 3'UTR 318. The downstream regulatory region may include a peptide tag such as the FLAG 3x tag. Each of these components is operably linked to the next, i.e., the inducible promoter is operably linked to the 5' end of the adhesion protein sequence encoding the cell adhesion protein, the cell adhesion protein coding sequence is operably linked to the 5' end of the fluorescent protein coding sequence. The fluorescent protein coding sequence is operably linked to the 5' end of the downstream regulatory region. The DNA construct IP-AP-FP-DRR is then integrated into a unicellular photosynthetic organism such as *Chlamydomonas reinhardtii* and organisms expressing the cell adhesion protein, including expression in the cell wall or extracellular matrix of the organism, are then generated.

Figure 4:
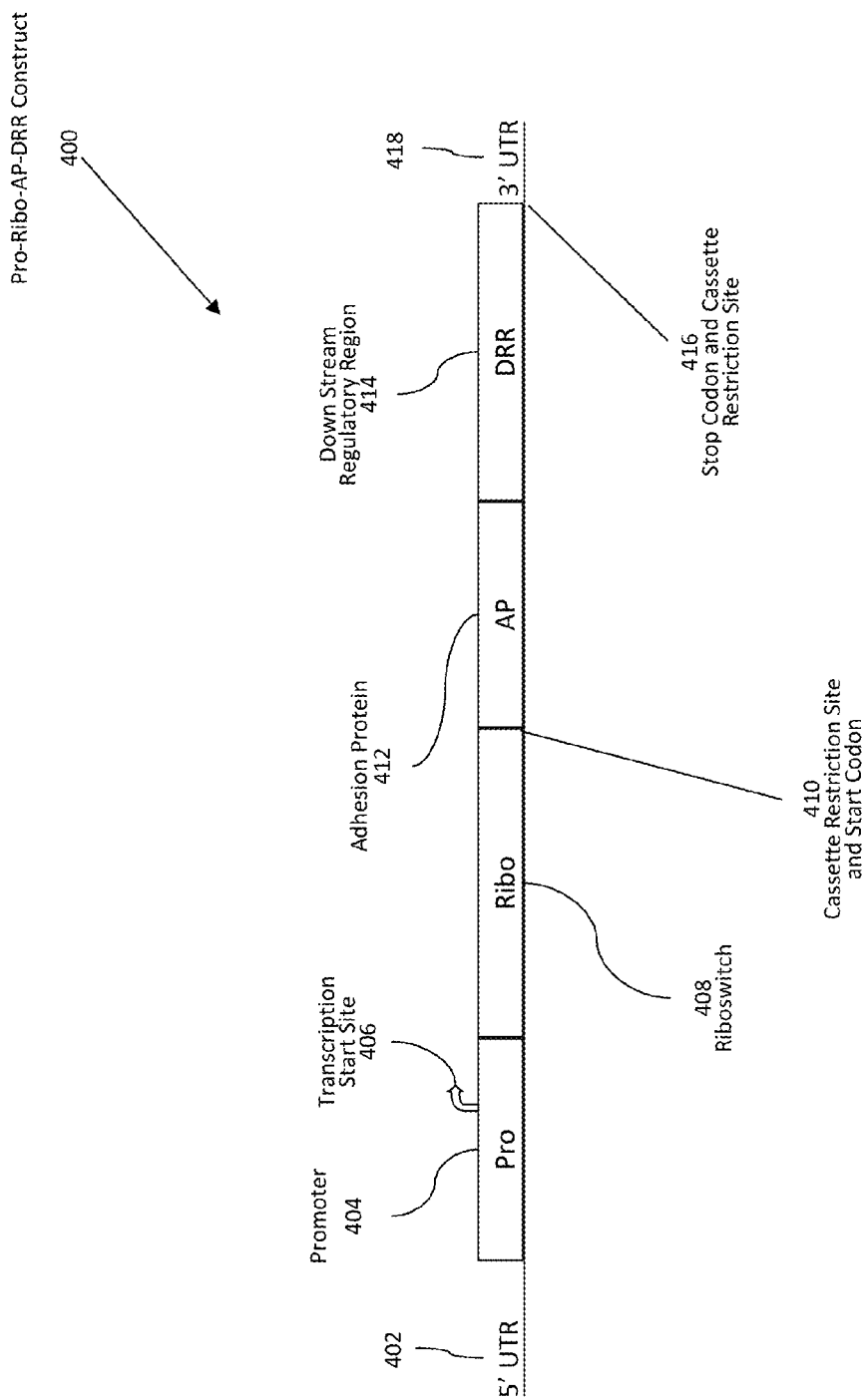
FIG. 4 is a map of a DNA construct, represented as Pro-Ribo-AP-DRR that includes (from 5' to 3'), a promoter, a riboswitch translation regulator, a cell adhesion protein coding sequence, and a downstream regulatory region.

As shown in FIG. 4, a construct is generally represented as Pro-Ribo-AP-DRR 400, where on the 5' UTR end 402 a promoter such as the PSAD promoter is provided as Pro 404 with a transcription start site 406. Ribo, 408 is a translational regulator such as THI4 riboswitch (SEQ ID NO:13). AP 412 is a cell adhesion protein such as the Algal-CAM, V1, V2, ISG, cadherin or claudin proteins with a restriction site and start codon 410 on the 5' end of the adhesion protein. The downstream regulatory region DRR 414 includes the transcription terminator sequence as well as the stop codon and 3' cassette restriction site 416 on the 3'UTR end 418. The downstream regulatory region may include a peptide tag such as the FLAG 3x tag. Each of these components is operably linked to the next, i.e., the promoter is operably linked to the 5' end of the translation regulation sequence. The translation regulation sequence is operably linked to the 5' end of the adhesion protein sequence encoding the cell adhesion protein. The cell adhesion protein coding sequence is operably linked to the 5' end of the downstream regulatory region. The DNA construct Pro-Ribo-AP-DRR is then integrated into a unicellular photosynthetic organism such as *Chlamydomonas reinhardtii* and organisms expressing the cell adhesion protein, including expression in the cell wall or extracellular matrix of the organism, are then generated.

Figure 5:
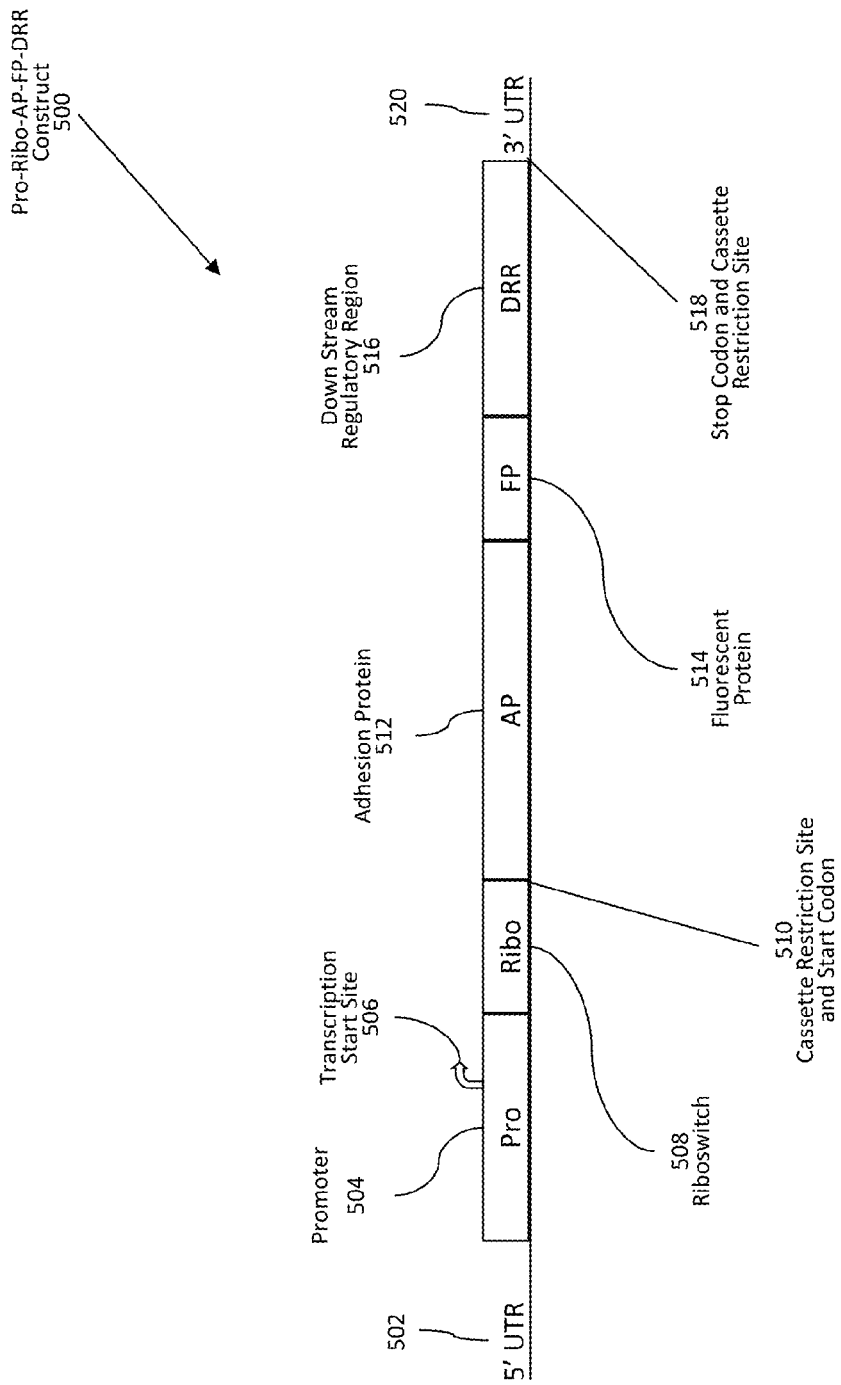
FIG. 5 is a map of a DNA construct, represented as Pro-Ribo-AP-FP-DRR that includes (from 5' to 3'), a promoter, a riboswitch translation regulator, a cell adhesion protein coding sequence, a fluorescent protein fusion coding sequence and a downstream regulatory region.

As shown in FIG. 5, a construct is generally represented as Pro-Ribo-AP-FP-DRR 500, where on the 5' UTR end 502 a promoter such as the PSAD promoter is provided as Pro 504 with a transcription start site 506. Ribo, 508 is a translational regulator such as the THI4 riboswitch. AP 512 is a cell adhesion protein such as the Algal-CAM, V1, V2, ISG, cadherin or claudin proteins with a restriction site and start codon 510 on the 5' end of the adhesion protein. FP 514 is a fluorescent fusion protein such as a yellow fluorescent protein (YFP), a cyan fluorescent protein (CFP), a red fluorescent protein (mRFP). The downstream regulatory region DRR 516 includes the transcription terminator sequence as well as the stop codon and 3' cassette restriction site 518 on the 3'UTR end 520. The downstream regulatory region may include a peptide tag such as the FLAG 3x tag. Each of these components is operably linked to the next, i.e., the promoter is operably linked to the 5' end of the translation regulation sequence. The translation regulation sequence is operably linked to the 5' end of the adhesion protein sequence encoding the cell adhesion protein. The cell adhesion protein coding sequence is operably linked to the 5' end of the fluorescent fusion protein coding sequence. The fluorescent fusion protein coding sequence is operably linked to the 5' end of the downstream regulatory region. The DNA construct Pro-Ribo-AP-FP-DRR is then integrated into a unicellular photosynthetic organism such as *Chlamydomonas reinhardtii* and organisms expressing the cell adhesion protein, including expression in the cell wall or extracellular matrix of the organism, are then generated.

Figure 6:
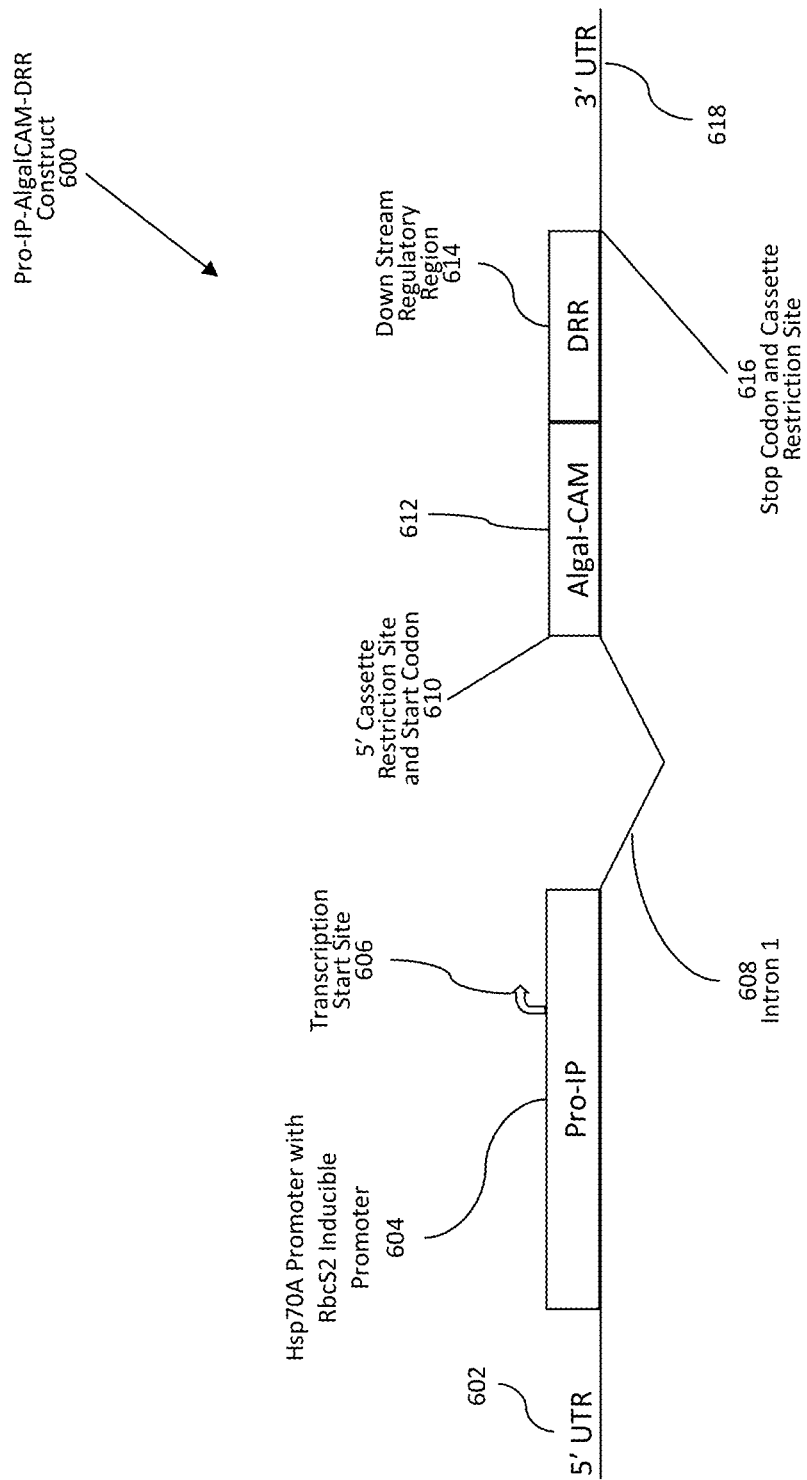
FIG. 6 is a map of a DNA construct, represented as Pro-IP-AlgalCAM-DRR that includes (from 5' to 3'), a promoter IP- with an inducible promoter, the Algal-CAM protein coding sequence, and a downstream regulatory region.

As shown in FIG. 6, a construct is generally represented as Pro-IP-AlgalCAM-DRR 600, where on the 5' UTR end 602 Pro-IP 604 is a promoter with an inducible promoter such as the RBCS2 promoter flanked by enhancer elements of HSP70A and RBCS2 intron 1 (SEQ ID NO:9) with an intron sequence coding sequence, Intron 1, 608 on the 3' end as well as a SacI restriction site on the 5' end with a transcription start site 606. AlgalCAM 612 is the Algal-CAM cell adhesion protein coding sequence (SEQ ID NO:2) with a restriction site and start codon 610 on the 5' end of the Algal-CAM protein coding sequence. The downstream regulatory region DRR 614 includes the transcription terminator sequence as well as the stop codon and 3' cassette restriction site 616 on the 3'UTR end 618. The downstream regulatory region may include a peptide tag such as the FLAG 3x tag. Each of these components is operably linked to the next, i.e., the Hsp70A/RbcS2 promoter with the Intron 1 sequence is operably linked to the 5'end of the Algal-CAM cell adhesion protein coding sequence encoding the cell adhesion protein. The cell adhesion protein coding sequence is operably linked to the 5' end of the downstream regulatory region. The DNA construct Pro-IP-AlgalCAM-DRR is then integrated into a unicellular photosynthetic organism such as *Chlamydomonas reinhardtii* and organisms expressing the cell adhesion protein are then generated.

Figure 7:
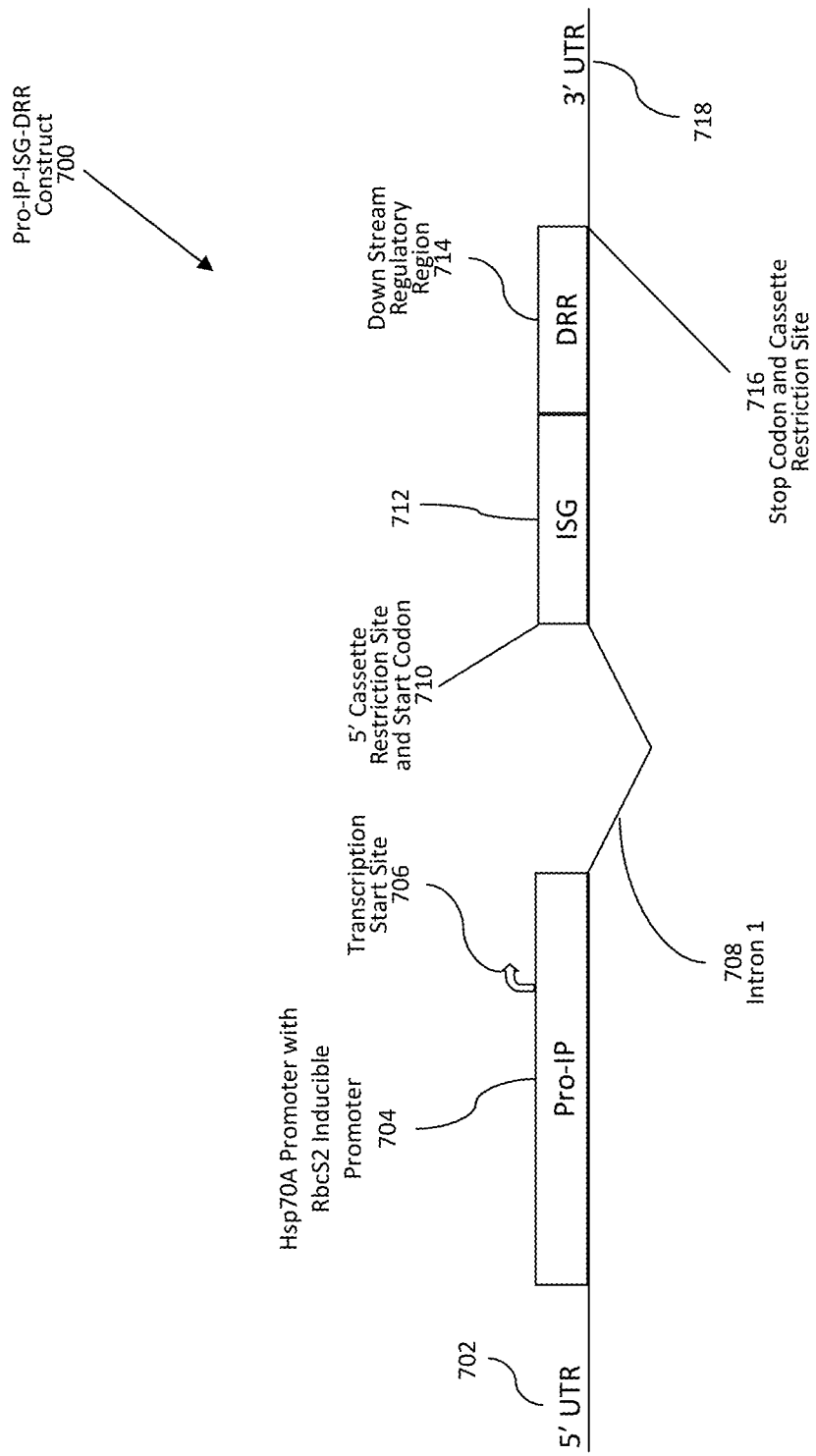
FIG. 7 is a map of a DNA construct, represented as Pro-IP-ISG-DRR that includes (from 5' to 3'), a promoter with an inducible promoter, the ISG protein coding sequence, and a downstream regulatory region.

As shown in FIG. 7, a construct is generally represented as Pro-IP-ISG-DRR 700, where on the 5' UTR end 702 Pro-IP 704 is a promoter with an inducible promoter such as the RBCS2 promoter flanked by enhancer elements of HSP70A and RBCS2 intron 1 (SEQ ID NO:9) with an intron sequence coding sequence, Intron 1, 708 on the 3' end as well as a SacI restriction site on the 5' end with a transcription start site 706. ISG (SEQ ID NO: 8) 712 is an inversion-specific glycoprotein coding sequence with a start codon of ATG 710 and a restriction site of NdeI at the 5' end of the ISG glycoprotein coding sequence. The downstream regulatory region DRR 714 includes the transcription terminator sequence as well as the stop codon and 3' cassette restriction site 716 on the 3'UTR end 718. The downstream regulatory region may include a peptide tag such as the FLAG 3x tag. Each of these components is operably linked to the next, i.e., the Hsp70A/RbcS2 promoter sequence with the Intron 1 sequence is operably linked to the 5'end of the ISG glycoprotein coding sequence encoding the cell adhesion protein. The ISG glycoprotein coding sequence is operably linked to the 5' end of the downstream regulatory region. The DNA construct Pro-IP-ISG-DRR is then integrated into a unicellular photosynthetic organism such as *Chlamydomonas reinhardtii* and organisms expressing the cell adhesion protein are then generated.

Figure 8:
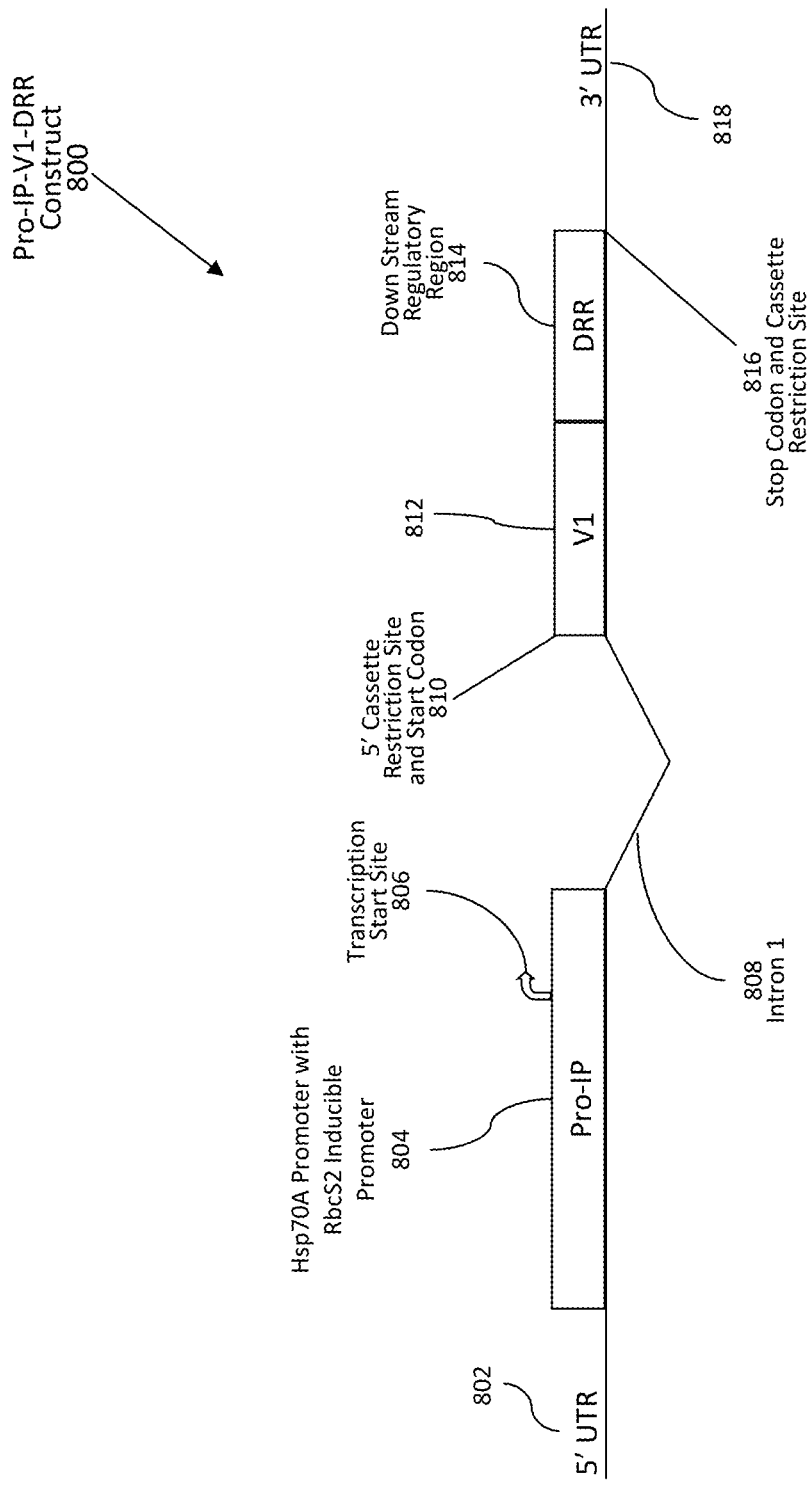
FIG. 8 is a map of a DNA construct, represented as Pro-IP-V1-DRR that includes (from 5' to 3'), a promoter with an inducible promoter, the V1 protein coding sequence, and a downstream regulatory region.

As shown in FIG. 8, a construct is generally represented as Pro-IP-V1-DRR 800, where on the 5' UTR end 802 Pro-IP 804 is a promoter with an inducible promoter such as the RBCS2 promoter flanked by enhancer elements of HSP70A and RBCS2 intron 1, 808 on the 3' end as well as a SacI restriction site on the 5' end with a transcription start site 806. V1 (SEQ ID NO:4) 812 is an extracellular HRGP extensin-related protein coding sequence with a start codon of ATG 810 and a restriction site of NdeI at the 5' end of the V1 coding sequence. The downstream regulatory region DRR 814 includes the transcription terminator sequence as well as the stop codon and 3' cassette restriction site 816 on the 3'UTR end 818. The downstream regulatory region may include a peptide tag such as the FLAG 3x tag. Each of these components is operably linked to the next, i.e., the Hsp70A/RbcS2 promoter sequence with the Intron 1 sequence is operably linked to the 5'end of the V1 extracellular HRGP extensin-related protein coding sequence encoding the cell adhesion protein. The V1 protein coding sequence is operably linked to the 5' end of the downstream regulatory region. The DNA construct Pro-IP-V1-DRR is then integrated into a unicellular photosynthetic organism such as *Chlamydomonas reinhardtii* and organisms expressing the cell adhesion protein are then generated.

Figure 9:
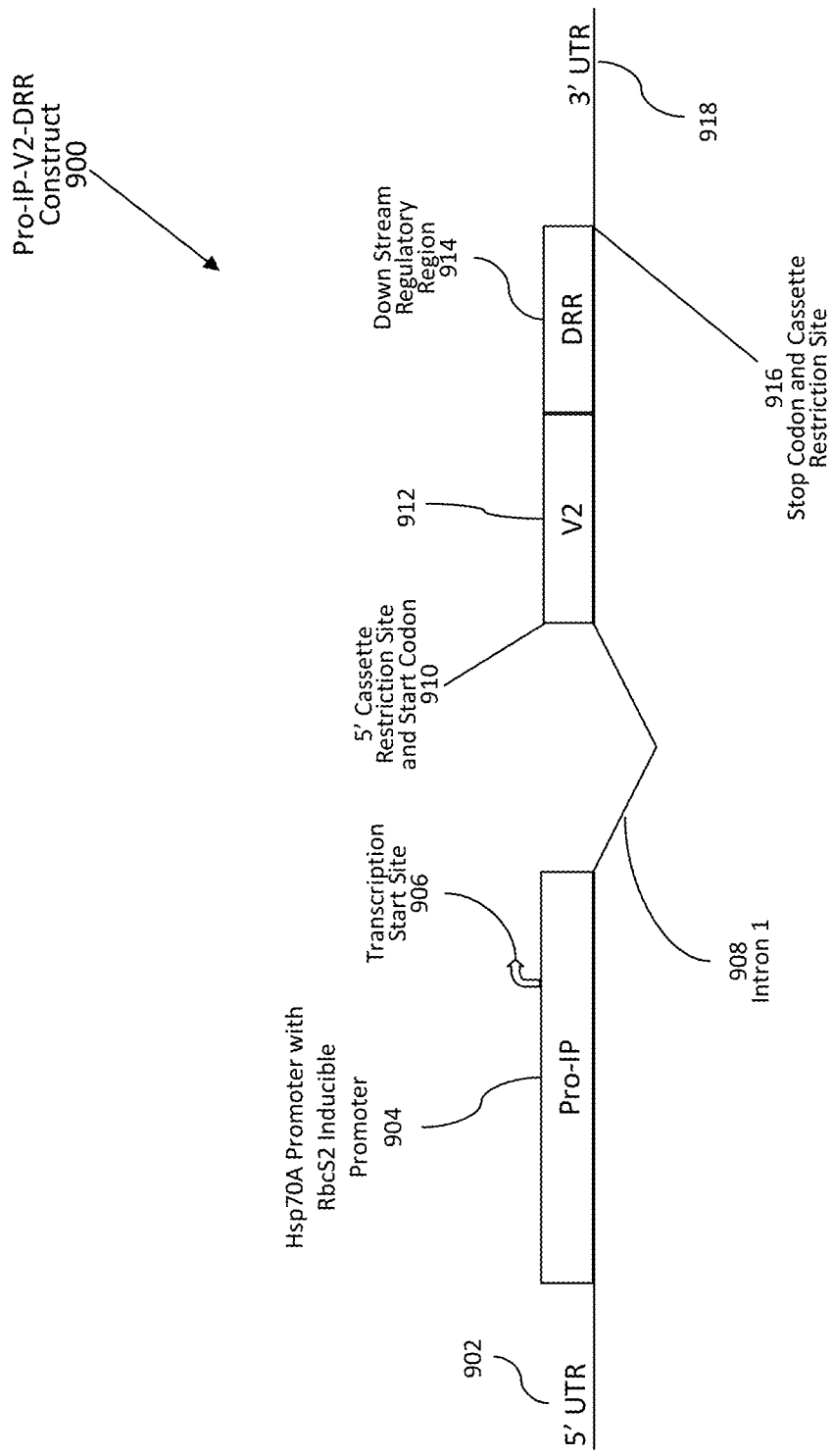
FIG. 9 is a map of a DNA construct, represented as Pro-IP-V2-DRR that includes (from 5' to 3'), a promoter with an inducible promoter, the V2 protein coding sequence, and a downstream regulatory region.

As shown in FIG. 9, a construct is generally represented as Pro-IP-V2-DRR 900, where on the 5' UTR end 902 Pro-IP 904 is a promoter with an inducible promoter such as the RBCS2 promoter flanked by enhancer elements of HSP70A and RBCS2 intron 1, 908 on the 3' end as well as a SacI restriction site on the 5' end with a transcription start site 906. V2 (SEQ ID NO:6) 912 is an extracellular HRGP extensin-related protein coding sequence with a start codon of ATG 910 and a restriction site of NdeI at the 5' end of the V2 coding sequence. The downstream regulatory region DRR 914 includes the transcription terminator sequence as well as the stop codon and 3' cassette restriction site 916 on the 3'UTR end 918. The downstream regulatory region may include a peptide tag such as the FLAG 3x tag. Each of these components is operably linked to the next, i.e., the Hsp70A/RbcS2 promoter sequence with the Intron 1 sequence is operably linked to the 5'end of the V2 extracellular HRGP extensin-related protein coding sequence encoding the cell adhesion protein. The V2 protein coding sequence is operably linked to the 5' end of the downstream regulatory region. The DNA construct Pro-IP-V2-DRR is then integrated into a unicellular photosynthetic organism such as *Chlamydomonas reinhardtii* and organisms expressing the cell adhesion protein are then generated.

Figure 10:
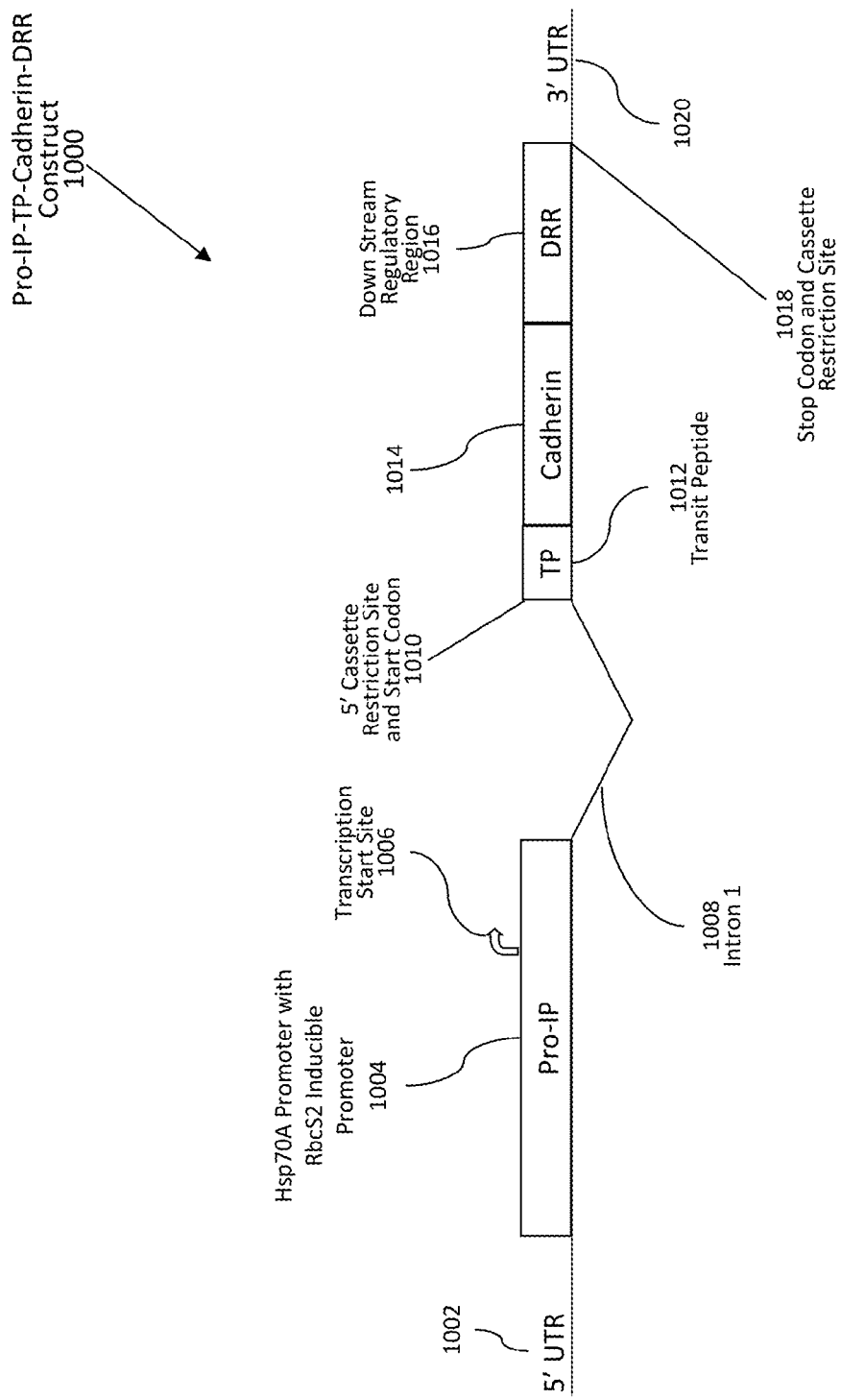
FIG. 10 is a map of a DNA construct, represented as Pro-IP-TP-Cadherin-DRR that includes (from 5' to 3'), a promoter with an inducible promoter, a transit peptide coding sequence, the cadherin protein coding sequence, and a downstream regulatory region.

As shown in FIG. 10, a construct is generally represented as Pro-IP-TP-Cadherin-DRR 1000, where on the 5' UTR end 1002, Pro-IP 1004 is a promoter with a inducible promoter such as the RBCS2 promoter flanked by enhancer elements of HSP70A and RBCS2 intron 1, 1008 on the 3' end as well as a SacI restriction site on the 5' end with a transcription start site 1006. TP 1012 is an algae specific transit peptide coding sequence, which directs transcription to the outer membrane or extracellular matrix of the algae. The transit peptide is operably linked to a cadherin protein coding sequence 1014 which is a calcium-dependent cell adhesion protein. Further, the cadherin protein fuses to the C-terminus of a catenin protein. The fusion domains between the cadherin protein and the catenin protein act to bind the cadherin to actin filaments of the cytoskeleton, which will cause flocculation or cell adhesion of the algae. The N-terminal domains of the cadherin protein are hemophilic and binds with the same adhesion scheme of Algal-CAM protein in that the protein is homophilic and thus binds to itself. The transit peptide has a start codon and a restriction site 1010 at the 5' end of the transit peptide coding sequence. The downstream regulatory region DRR 1016 includes the transcription terminator sequence as well as the stop codon and 3' cassette restriction site 1018 on the 3'UTR end 1020. The downstream regulatory region may include a peptide tag such as the FLAG 3x tag. Each of these components is operably linked to the next, i.e., the Hsp70A/RbcS2 promoter sequence with the Intron 1 sequence is operably linked to the 5'end of the transit peptide. The transit peptide is operably linked to the 5' end of the cadherin protein. The cadherin protein coding sequence is operably linked to the 5' end of the downstream regulatory region. The DNA construct Pro-IP-TP-Cadherin-DRR is then integrated into a unicellular photosynthetic organism such as *Chlamydomonas reinhardtii* where the cell wall of the organism has been removed by means of an induced mutation, fusing an enzyme to the organism or fusing a cell wall degrading enzyme to the cadherin DNA construct Pro-IP-TP-Cadherin-DRR. Organisms expressing the cadherin cell adhesion protein, including expression in the outer membrane or extracellular matrix, are then generated.

Figure 11:
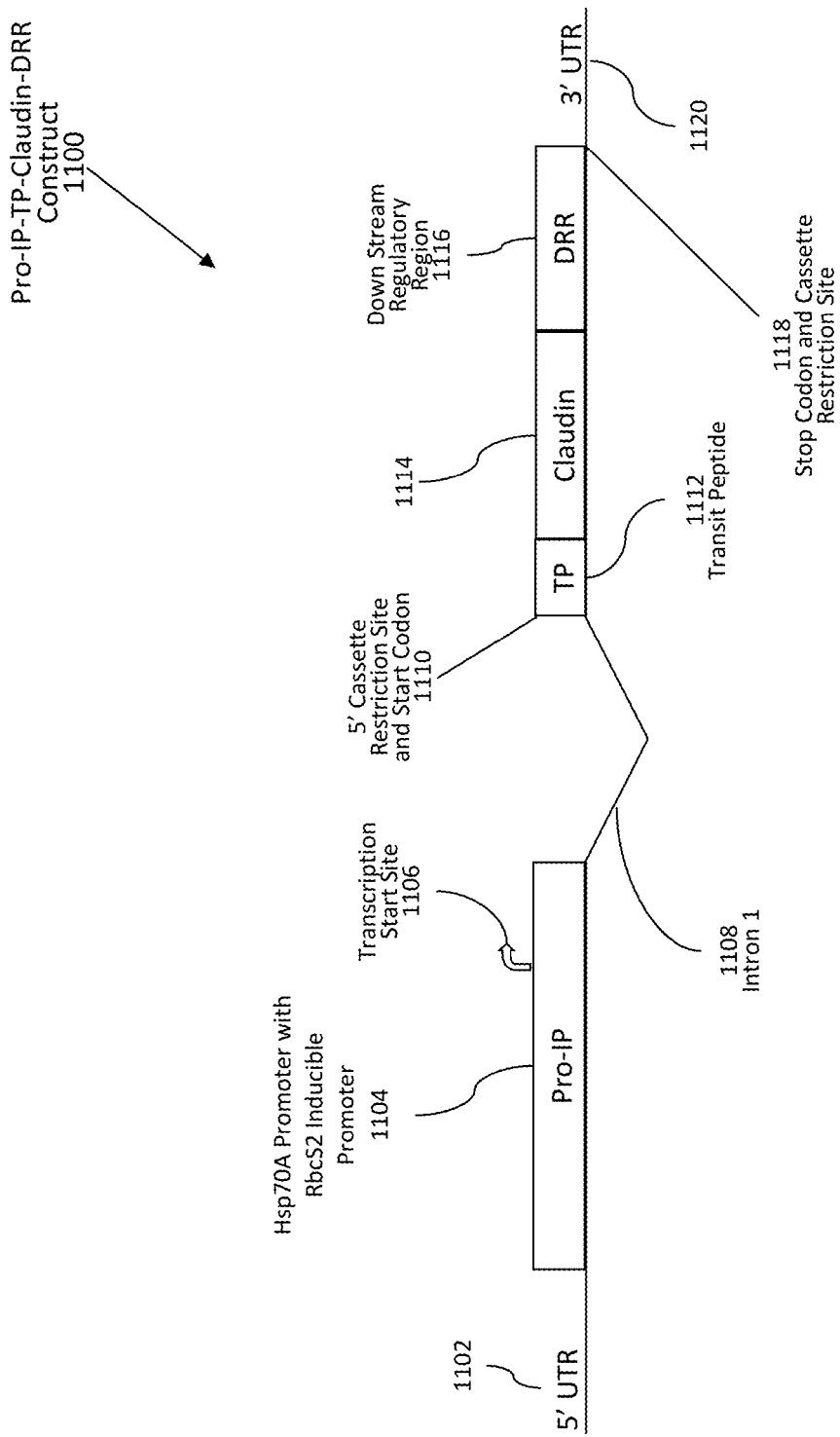
FIG. 11 is a map of a DNA construct, represented as Pro-IP-TP-Claudin-DRR that includes (from 5' to 3'), a promoter with an inducible promoter, a transit peptide coding sequence, the claudin protein coding sequence, and a downstream regulatory region.

As shown in FIG. 11, a construct is generally represented as Pro-IP-TP-Claudin-DRR 1100, where on the 5' UTR end 1102 Pro-IP 1104 is a promoter with an in inducible promoter, such as the RBCS2 promoter flanked by enhancer elements of HSP70A and RBCS2 intron 1, 1108 on the 3' end as well as a SacI restriction site on the 5' end with a transcription start site 1106. TP 1112 is an algae specific transit peptide coding sequence, which directs transcription to the outer membrane or extracellular matrix of the organism. The transit peptide coding sequence is operably linked to a claudin transmembrane protein coding sequence 1114. The transit peptide has a start codon and a restriction site 1110 at the 5' end of the transit peptide coding sequence. The downstream regulatory region DRR 1116 includes the transcription terminator sequence as well as the stop codon and 3' cassette restriction site 1118 on the 3'UTR end 1120. The downstream regulatory region may include a peptide tag such as the FLAG 3x tag. Each of these components is operably linked to the next, i.e., the Hsp70A/RbcS2 promoter sequence with the Intron 1 sequence is operably linked to the 5'end of the transit peptide. The transit peptide is operably linked to the 5' end of the claudin protein. The claudin protein coding sequence is operably linked to the 5' end of the downstream regulatory region. The DNA construct Pro-IP-TP-Claudin-DRR is then integrated into a unicellular photosynthetic organism such as *Chlamydomonas reinhardtii* where the cell wall of the organism has been removed using by means of induced mutation, fusing an enzyme to the organism or fusing a cell wall degrading enzyme to the claudin DNA construct Pro-IP-TP-Claudin-DRR. Organisms expressing the claudin cell adhesion protein including expression in the outer membrane or extracellular matrix, are then generated.

Figure 12:
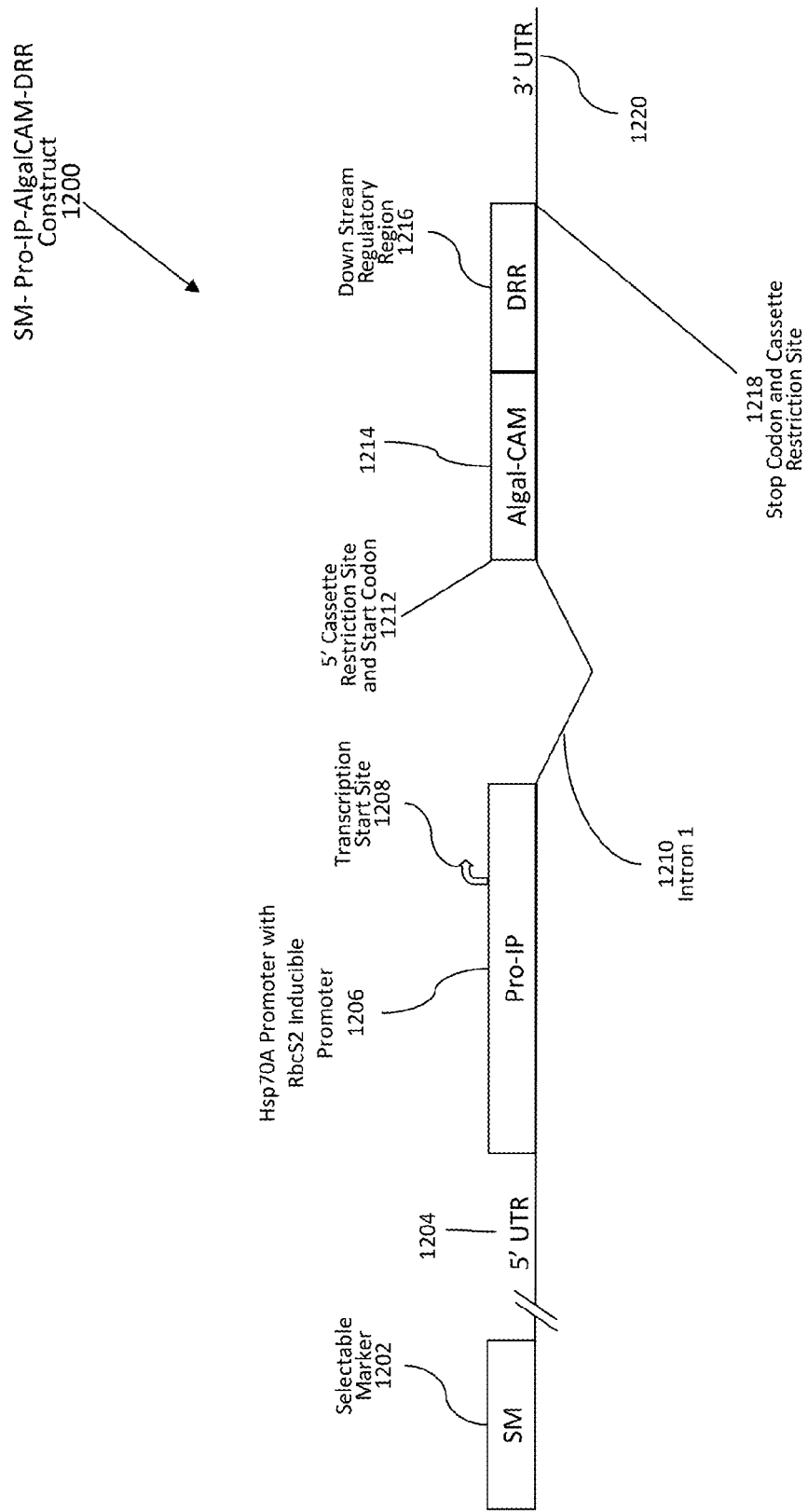
FIG. 12 is a map of a DNA construct, represented as SM-Pro-IP-AlgalCAM-DRR that includes (from 5' to 3') a selectable marker, a promoter with an inducible promoter, the Algal-CAM protein coding sequence, and a downstream regulatory region.

As shown in FIG. 12, a construct is generally represented as SM-Pro-IP-AlgalCAM-DRR 1200, where SM 1202 is a selectable marker on the 5' UTR end 1204. Pro-IP 1206 is a RBCS2 inducible promoter sequence and a HSP70A constitutive inducible promoter sequence with an intron sequence coding sequence, Intron 1, 1210 on the 3' end as well as a SacI restriction site on the 5' end with a transcription start site 1208. AlgalCAM 1214 is the Algal-CAM cell adhesion protein coding sequence with a restriction site and start codon 1212 on the 5' end of the Algal-CAM protein coding sequence. The downstream regulatory region DRR 1216 includes the transcription terminator sequence as well as the stop codon and 3' cassette restriction site 1218 on the 3'UTR end 1220. The downstream regulatory region may include a peptide tag such as the FLAG 3x tag. Each of these components is operably linked to the next, i.e., the selectable marker is operably linked to the Hsp70A/RbcS2 promoter sequence with the Intron 1 sequence. The Hsp70A/RcS2 promoter sequence is operably linked to the 5'end of the Algal-CAM protein coding sequence. The Algal-CAM protein coding sequence is operably linked to the 5' end of the downstream regulatory region. The DNA construct SM-Pro-IP-Algal-CAM-DRR is then integrated into a unicellular photosynthetic organism such as *Chlamydomonas reinhardtii* and organisms expressing the cell adhesion protein are then generated.

Generally, the DNA that is introduced into an organism is part of a construct. A construct is an artificially constructed segment of DNA that may be introduced into a target organism tissue or organism cell. The DNA may be a gene of interest, e.g., a coding sequence for a protein, or it may be a sequence that is capable of regulating expression of a gene, such as an antisense sequence, a sense suppression sequence, or a miRNA sequence. As used herein, "gene" refers to a segment of nucleic acid. A gene can be introduced into a genome of a species, whether from a different species or from the same species. The construct typically includes regulatory regions operably linked to the 5' side of the DNA of interest and/or to the 3' side of the DNA of interest. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. A cassette containing all of these elements is also referred to herein as an expression cassette. The expression cassettes may additionally contain 5' leader sequences in the expression cassette construct. (A leader sequence is a nucleic acid sequence containing a promoter as well as the upstream region of a gene.) The regulatory regions (i.e., promoters, transcriptional regulatory regions, translational regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. The expression cassette may additionally contain selectable marker genes.

The expression cassette may additionally contain selectable marker genes. Targeting constructs are engineered DNA molecules that encode genes and flanking sequences that enable the constructs to integrate into the host genome at (targeted) locations. Publicly available restriction proteins may be used for the development of the constructs. Targeting constructs depend upon homologous recombination to find their targets.

The expression cassette or chimeric genes in the transforming vector typically have a transcriptional termination region at the opposite end from the transcription initiation regulatory region. The transcriptional termination region may normally be associated with the transcriptional initiation region from a different gene. The transcriptional termination region may be selected, particularly for stability of the mRNA, to enhance expression. Illustrative transcriptional termination regions include the NOS terminator from *Agrobacterium* Ti plasmid and the rice α-amylase terminator. A promoter is a DNA region, which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. The promoter may be any DNA sequence, which shows transcriptional activity in the chosen plant cells, plant parts, or plants. The promoter may be inducible or constitutive. It may be naturally-occurring, may be composed of portions of various naturally-occurring promoters, or may be partially or totally synthetic. Guidance for the design of promoters is provided by studies of promoter structure. Also, the location of the promoter relative to the transcription start may be optimized. Many suitable promoters for use in algae, plants, and photosynthetic bacteria are well known in the art, as are nucleotide sequences, which enhance expression of an associated expressible sequence.

Promoters

While the PSAD constitutive promoter (SEQ ID NO:10) and the riboswitch translational regulator (SEQ ID NO:13) or the regulatory region upstream of the protein coding sequences are two examples of promoters that may be used, a number of promoters may be used, including but not limited to the RBCS2 promoter flanked by enhancer elements of HSP70A and RBCS2 intron 1 (SEQ ID NO:9), the RBCS2 inducible promoter and the HSP70A inducible promoter and transcription processing improvement sequences as well as the NIT1 promoter (induced upon nitrogen depletion) the CA1 promoter, and the CYC6 promoter. Promoters can be selected based on the desired outcome. That is, the nucleic acids can be combined with constitutive, tissue-preferred, or other promoters for expression in the host cell of interest. The promoter may be inducible or constitutive. It may be naturally-occurring, may be composed of portions of various naturally-occurring promoters, or may be partially or totally synthetic. In addition, the location of the promoter relative to the transcription start may be optimized. Many suitable promoters for use in algae, plants, and photosynthetic bacteria are well known in the art, as are nucleotide sequences, which enhance expression of an associated expressible sequence.

Algal-CAM Protein

Adhesion of cells in *V. carteri* is primarily mediated by glycoproteins, one of which is designated Algal-CAM (SEQ ID NO:1 and SEQ ID NO:2). Algal-CAM is made up of three primary structural domains: an N-terminal extensin-like domain and two C-terminal fasciclin I domains. The N-terminal extensin-like domain belongs to a family of rod shaped hydroxyproline-rich glycoprotein (HRGP) domains found within the cell wall or extracellular matrix of *V. carteri, C. reinhardtii*, other green algae, and higher plants. In *C. reinhardtii* and higher plants, extensin domains are known to become insolubilized upon secretion to the hydroxyproline-enriched extracellular matrix by covalent isodityrosine cross-linking. Fasciclin I domains are known to mediate cell-cell adhesion by homophilic binding interactions. The combination of a wall anchoring extensin domain and homophilic fasciclin I domains allow Algal-CAM to bind the cell walls or extracellular matrix of adjacent *V. carteri* cells together.

Inversion-Specific Glycoprotein (ISG)

ISG (SEQ ID NO:7 and SEQ ID NO:8) is a development-specific cell wall glycoprotein that is involved in cell adhesion during the inversion stage of *Volvox* sp. embryonic development. Prior to inversion, the cell wall of *Volvox* embryos is nearly absent and their cells are held together by cytoplasmic bridges. During inversion, the cytoplasmic bridges disintegrate and ISG is expressed, though only for a few minutes. ISG molecules hold *Volvox* cells together during inversion but also form a preliminary matrix to which subsequent cell wall elements are added as the post-inversion *Volvox* colony develops the thick, complex cell wall characteristic of *Volvox* at maturity. Expression of ISG is a necessary first step to engineering a *Volvox*-like cell wall in *Chlamydomonas* that can hold cells together in a robust, multicellular structure. ISG consists of a C-terminal rod-shaped extensin domain fused to an N-terminal globular domain. The most C-terminal portion of ISG includes a unique patch of positively charged residues situated close to an adjacent patch of negatively charged residues. The structure and charge distribution of ISG allow it to form branched networks with itself and other cell wall elements that serve as a molecular scaffold for other cell wall components as they are secreted. ISG occurs in the BZ3 layer of the *Volvox* cell wall, which is functionally equivalent to the *Chlamydomonas* W2 layer. ISG is a key organizer for *Volvox* cell wall development because the W2 wall layer in *Chlamydomonas* is also known to nucleate and organize its cell wall.

Pherophorins V1 and V2

While Algal-CAM alone causes some degree of cell adhesion in *Chlamydomonas*, the use of "pherophorins" proteins (V1 and V2) (SEQ ID NO:3; SEQ ID NO: 4; SEQ ID NO:5 and SEQ ID NO:6) of *Volvox* act are effective multicellularity inducers in their own right. Pherophorins are a family of hydroxyproline-rich glycoprotein (HRGP) extensin-related proteins present in the *Volvox* cell wall. Pherophorins V1 and V2 are especially important for repair of physical damage to the *Volvox* cell wall. Expression of these proteins in *Chlamydomonas* adds the bulk meshwork needed for an expanded, *Volvox*-like cell wall. V1 and V2 structures closely resemble that of ISG but with two distinctions: (i) the rod-shaped extensin domain has slightly different repeat motifs and (ii) it is flanked on each end by globular lectin domains, giving V1 and V2 a dumbbell-shaped conformation. HRGPs with this conformation are thought to form complex, intermolecular meshworks, with mesh size determined by length of the extensin domain. The globular domains of pherophorins bind end-to-end and also side-to-side, resulting in a complex proteinaceous matrix similar to type I and IV collagens.

Cadherin Proteins

Cadherin proteins are a group of calcium-dependent cell adhesion proteins. Cadherin proteins promote cell adhesion through homophilic interactions. N (neural)-cadherin is predominantly expressed by neural cells, endothelial cells and a variety of cancer cell types. E (epithelial)-cadherin is predominantly expressed by epithelial cells. Other cadherins are P (placental)-cadherin, which is found in human skin and R (retinal)-cadherin. A transit peptide (TP) is a peptide coding sequence that is operably linked to a protein such as the cadherin protein in order to facilitate translation or direct translation of the protein to a specific location in the organism of interest.

Claudin proteins are a family of transmembrane proteins with binding domains that are important in formation of cell junctions. The cell junctions that claudin proteins create control cell transport and cell polarity as well as cell permeability.

Vector Construction, Transformation, and Heterologous Protein Expression

As used herein plasmid, vector or cassette refers to an extrachromosomal element often carrying genes and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a cell.

An example of an expression vector is a *Chlamydomonas* expression vector designated pSI105. Derivatives of the vectors described herein may be capable of stable transformation of many photosynthetic unicells, including but not limited to unicellular algae of many species, photosynthetic bacteria, and single photosynthetic cells, protoplasts, derived from the green parts of plants as well as cyanobacteria including but not limited to *Arthrospira* spp., *Spirulina* spp., *Synechococcus elongatus* 7942, *Synechococcus* spp., *Synechosystis* spp. PCC 6803, *Synechosystis* spp., *Spirulina plantensis, H. salinarum, Calothrix* spp., *Anabaena flos-aquae, Aphanizomenon* spp., *Anadaena* spp., *Gleotrichia* spp., *Oscillatoria* spp. and *Nostoc* spp., eukaryotic unicellular algae such as but not limited to *Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococ-* cus spp., *Isochrysis* spp., *Laminaria* spp., *Nannochloropsis* spp., *Navicula* spp., *Pleurochrysis* spp. and *Sargassum* spp.

Vectors for stable transformation of algae, bacteria, and plants are well known in the art and can be obtained from commercial vendors. Expression vectors can be engineered to produce heterologous and/or homologous protein(s) of interest (e.g., antibodies, mating type agglutinins, etc.). Such vectors are useful for recombinantly producing the protein of interest. Such vectors are also useful to modify the natural phenotype of host cells (e.g., expressing a cell adhesion protein).

To construct the vector, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing the region responsible for encoding the gene's protein but leaving the upstream region found to contain the genetic material responsible for control of the gene's expression. A synthetic oligonucleotide is preferably inserted in the location where the protein sequence once was, such that any additional gene could be cloned in using restriction endonuclease sites in the synthetic oligonucleotide (i.e., a multicloning site). An unrelated gene (or coding sequence) inserted at this site would then be under the control of an extant start codon and upstream regulatory region that will drive expression of the foreign (i.e., not normally present) protein encoded by this gene. Once the gene for the foreign protein is put into a cloning vector, it can be introduced into the host organism using any of several methods, some of which might be particular to the host organism. Variations on these methods are described in the general literature. Manipulation of conditions to optimize transformation for a particular host is within the skill of the art.

The basic transformation techniques for transgene expression in photosynthetic unicells are commonly known in the art. These methods include, for example, introduction of plasmid transformation vectors or linear DNA by use of cell injury, by use of biolistic devices, by use of a laser beam or electroporation, by microinjection, or by use of *Agrobacterium tumifaciens* for plasmid delivery with transgene integration or by any other method capable of introducing DNA into a host cell.

The basic techniques used for transformation and transgene expression in photosynthetic organisms are known in the art. These methods have been described in a number of texts for standard molecular biological manipulation. These methods include, for example, use of a laser beam, electroporation, microinjection or any other method capable of introducing DNA into a host cell (e.g., an NVPO).

Other transformation methods are available to those skilled in the art, such as direct uptake of foreign DNA constructs, techniques of electroporation or high-velocity ballistic bombardment with metal particles coated with the nucleic acid constructs.

To confirm the presence of the transgenes in transgenic cells, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic organisms have been obtained, they may be grown to produce organisms or parts having the desired phenotype.

Use of a Selectable Marker (SM)

A selectable marker can provide a means to obtain prokaryotic cells or plant cells or both that express the marker and, therefore, can be useful as a component of a vector. Examples of selectable markers include, but are not limited to, those that confer antimetabolite resistance, for example, dihydrofolate reductase, which confers resistance to methotrexate; neomycin phosphotransferase, which confers resistance to the aminoglycosides neomycin, kanamycin and paromycin (SEQ ID NO:11 and SEQ ID NO:12); hygro, which confers resistance to hygromycin, trpB, which allows cells to utilize indole in place of tryptophan; hisD, which allows cells to utilize histinol in place of histidine; mannose-6-phosphate isomerase which allows cells to utilize mannose; ornithine decarboxylase, which confers resistance to the ornithine decarboxylase inhibitor, 2-(difluoromethyl)-DL-ornithine; and deaminase from *Aspergillus terreus*, which confers resistance to Blasticidin S. Additional selectable markers include those that confer herbicide resistance, for example, phosphinothricin acetyltransferase gene, which confers resistance to phosphinothricin, a mutant EPSPV-synthase, which confers glyphosate resistance, a mutant acetolactate synthase, which confers imidazolione or sulfonylurea resistance, a mutant psbA, which confers resistance to atrazine, or a mutant protoporphyrinogen oxidase, or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants.

Fluorescent peptide (FP) fusions allow analysis of dynamic localization patterns in real time. Over the last several years, a number of different colored fluorescent peptides have been developed and may be used in various constructs, including yellow FP (YFP), cyan FP (CFP), red FP (mRFP) and others. Some of these peptides have improved spectral properties, allowing analysis of fusion proteins for a longer period of time and permitting their use in photobleaching experiments. Others are less sensitive to pH, and other physiological parameters, making them more suitable for use in a variety of cellular contexts. Additionally, FP-tagged proteins can be used in protein-protein interaction studies by bioluminescence resonance energy transfer (BRET) or fluorescence resonance energy transfer (FRET). High-throughput analyses of FP fusion proteins in *Arabidopsis* have been performed by overexpressing cDNA-GFP fusions driven by strong constitutive promoters. A standard protocol is to insert the mRFP tag or marker at a default position of ten amino acids upstream of the stop codon, following methods established for *Arabidopsis*. Although useful, this approach has inherent limitations, as it does not report tissue-specificity, and overexpression of multimeric proteins may disrupt the complex. Furthermore, overexpression can lead to protein aggregation and/or mislocalization.

In order to tag a specific gene with a fluorescent peptide such as the red fluorescent protein (mRFP), usually a gene ideal for tagging has been identified through forward genetic analysis or by homology to an interesting gene from another model system. For generation of native expression constructs, full-length genomic sequence is required. For tagging of the full-length gene with an FP, the full-length gene sequence should be available, including all intron and exon sequences. A standard protocol is to insert the mRFP tag or marker at a default position of ten amino acids upstream of the stop codon, following methods known in the art established for *Arabidopsis*. The rationale is to avoid masking C-terminal targeting signals (such as endoplasmic reticulum (ER) retention or peroxisomal signals). In addition, by avoiding the N-terminus, disruption of N-terminal targeting sequences or transit peptides is avoided. However, choice of tag insertion is case-dependent, and it should be based on information on functional domains from database searches. If a homolog of the gene of interest has been successfully tagged in another organism, this information is also used to choose the optimal tag insertion site. A flexible linker peptide may be placed between proteins such that the desired protein is obtained. A cleavable linker peptide may also be placed between proteins such that they can be cleaved and the desired protein obtained. An example of a flexible linker may include (GSS)2, which is a flexible linker added by the reverse primer using the primers Fwdw/BglII (SEQ ID NO:19) and Revw/MscI (SEQ ID NO:20) or Revw/MscI and linker (SEQ ID NO:21).

Transcription Terminator

The transcription termination region of the constructs is a downstream regulatory region including the stop codon TGA and the transcription terminator sequence. Alternative transcription termination regions which may be used may be native with the transcriptional initiation region, may be native with the DNA sequence of interest, or may be derived from another source. The transcription termination region may be naturally occurring, or wholly or partially synthetic. Convenient transcription termination regions are available from the Ti-plasmid of *Agrobacterium tumefaciens*, such as the octopine synthase and nopaline synthase transcription termination regions or from the genes for beta-phaseolin, the chemically inducible plant gene, pIN.

The practice described herein employs, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., *Molecular Cloning, 2nd Ed.*, Cold Spring Harbor Laboratory Press, Cold Spring Harbor, N.Y. (1989); Sambrook and Russell, *Molecular Cloning, 3rd Ed.*, Cold Spring Harbor Laboratory Press, Cold Spring Harbor, N.Y. (2001); Ausubel, et al., *Current Protocols in Molecular Biology*, John Wiley & Sons (including periodic updates) (1992); Glover, DNA Cloning, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, Methods In Enzymology, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology: From Basic Science to Drug Development*, Cambridge University Press, Cambridge (2005); Schepers, *RNA Interference in Practice*, Wiley VCH (2005); Engelke, *RNA Interference (RNAi): The Nuts & Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004)).

EXAMPLES

The following examples are provided to illustrate further the various applications and are not intended to limit the invention beyond the limitations set forth in the appended claims.

Example 1

Algal-CAM Construct in *Chlamydomonas* or Other Unicellular Algae

In at least one embodiment is provided a unicellular microalgae capable of expression of the Algal-CAM gene. Green algae were acquired from the UTEX culture collection and the *Chlamydomonas* Center culture collection. *Volvox carteri* f. *nagariensis* (UTEX#1886) was cultured in 0.5× Bolds Modified medium with 0.5× supplemental soil water supernatant. Arginine auxotroph cell wall mutants of *C. reinhardtii* (Δ Arg7 cw-15, CC-425) were used for all *Chlamydomonas* experiments and were grown in TAP or TAP+yeast extract with rotary shaking at 140 rpm under continuous fluorescent light of 60 µmol photons m-2s-1.

Qiagen Plant RNeasy RNA Extraction Kits (#74903) with "Shredder" columns were used as recommended by the manufacturer starting with 3-5×106 total cells. For *V. carteri* cells, the liquid N2 lysis method was used with RNase-free disposable pestles and 1.7 ml tubes. Buffer RLT and the Shredder columns were sufficient to lyse and homogenize *C. reinhardtii* cells. DNase treatment of RNA samples was carried out to eliminate genomic DNA contamination with DNase I, as recommended by the manufacturer. cDNA synthesis was carried out directly after RNA extraction and DNase treatment using the SuperScript III First-Strand Synthesis SuperMix kit as recommended by the manufacturer using oligo(dT)20 primers.

Standard recombinant DNA techniques were used to generate all constructs. The 1,323 bp Algal-CAM CDS (SEQ ID NO:2) was amplified from *V. carteri* cDNA preparations using Phusion HF DNA polymerase per the manufacturer's recommendations with oligonucleotides ACAMCDS2fwd (SEQ ID NO:15) and ACAMCDS2rev (SEQ ID NO:16). This CDS corresponds to the open reading frame encoded by the cam1 mRNA splice variant 2 of Algal-CAM which incorporates the C-terminal exon VIII and not the GPI associated exon IX. The Algal-CAM CDS was cloned into pCR-TOPO-2.1 as recommended by the manufacturer and confirmed by sequencing using the M13 primer pair. A *C. reinhardtii* codon-optimized green fluorescent protein sequence (cGFP) was amplified similarly using primer pairs FwdxhoIBglII (SEQ ID NO:17) and RevBamHI (SEQ ID NO:18)] from pKscGFP as an XhoI/BamHI amplicon with a BglII site inserted in-between the XhoI and MscI sites by the forward primer and ligated into pRbcRL(Hsp196) using the XhoI/BamHI sites to create pRbcGFP(Hsp196). pRbcGFP (Hsp196) is a derivative of pRbcRL(Hsp196) but with a *C. reinhardtii* codon-optimized GFP sequence inserted in place of the luciferase sequence. The expression vector, pRbcRL (Hsp196), and it's derivatives drive transcription using a truncated RBCS2 promoter flanked by enhancer elements of HSP70A and RBCS2 intron 1 (SEQ ID NO:9). Algal-CAM was subcloned in-frame and upstream of the cGFP in pRbcGFP(Hsp196) as a BglII/MscI fragment by amplification with primers that added a 5'BglII site, a 3'MscI site and removed the stop codon. In the case of derivative RbcGFP-ACAMwL, a flexible linker, (GSS)2, was added by the reverse primer using the primers Fwdw/BglII (SEQ ID NO:19) and Revw/MscI (SEQ ID NO: 20) or Revw/MscI and linker (SEQ ID NO:21). This resulted in the sequence-verified constructs pRbcGFP-ACAM (SEQ ID NO:14), with no linker, and pRbcGFP-ACAMwL, with linker added.

Co-transformation using pArg7 and either pRbcGFP-ACAM or pRbcGFP-ACAMwL was carried out according to the nuclear glass bead method using cells at 2-6×106 cells/ml. Arginine prototrophs were selected on TAP without arginine and screened for transgene presence via PCR of the transgene with primers amplifying a recombinant 598 bp region spanning the cGFP sequence and the ACAM sequence: Scnfwd1 (SEQ ID NO:22) and Scnrev1 (SEQ ID NO:23). Colonies were further screened for mRNA expression via RT-PCR or flocculation phenotype or both. Genomic DNA was extracted by incubating cells at 100° C. for 5 min in 10 mM NaEDTA followed by centrifugation.

Template cDNA preparations were screened with primers amplifying a 453 bp recombinant region of the transgene that spanned the promoter region and the Algal-CAM region: ScnRTPCRfwd2 (SEQ ID NO:24) and ScnRTPCRrev2 (SEQ ID NO:25). Primers directed toward cActin mRNA were intron-spanning and amplified an mRNA-derived cDNA target of 344 bp: cActinfwd1 (SEQ ID NO:26) and cActinrev1 (SEQ ID NO:27). The cActin amplification was used as a positive mRNA/constitutive loading control. Recommended PCR reaction conditions were used with Phusion HF DNA polymerase with annealing temp of 58° C. for 35 cycles. PCR amplicons were separated on 2% TAE agarose gels stained with ethidium bromide.

100 µl of 72 hr liquid culture was used to inoculate 3 ml of medium in 12 well culture plates that were grown for 24 hours in the light with shaking. Low magnification micrographs were then taken in the 12 well plates using an inverted Leica DMI3000 B microscope with a 2.5× objective after separating individual flocs by gentle rotary agitation. Higher magnification fluorescence micrographs were taken using a Zeiss 710 scanning confocal laser microscope at 63× magnification, 488 nm excitation, and 510 nm emission.

300 ul of 72 hr liquid culture was used to inoculate 5 ml of medium in 50 ml culture tubes and grown for 72 hours under light with shaking. Cultures were vortexed and photographed. Cultures were then left to settle for 10 min and photographed again.

Prototroph genomic DNA was screened for presence of the transgene with primers amplifying a 598 bp amplicon spanning the Algal-CAM-cGFP fusion site. Presence of the Algal-CAM transgene was confirmed in approximately 20% of the transformant colonies. Roughly 50 transformants per transformation were screened for the Algal-CAM transgene presence using this PCR screening process.

Prototroph colonies showing positive results from the PCR screen of genomic DNA were further analyzed using RT-PCR to screen for mRNA expression. RT-PCR primers amplified a region of the transgene that spans the promoter and Algal-CAM fusion site.

As soon as prototroph colonies expressing Algal-CAM were cultured in liquid, varying degrees of flocculation were observed in comparison to the background strain (Δ Arg7 cw-15). The transgenic strains formed large flocculations ranging from 800 µm to 1,700 µm in diameter that tended to loosely adhere to each other and settle to the bottom of the culture in 10 minutes or less after shaking.

Figure 13:
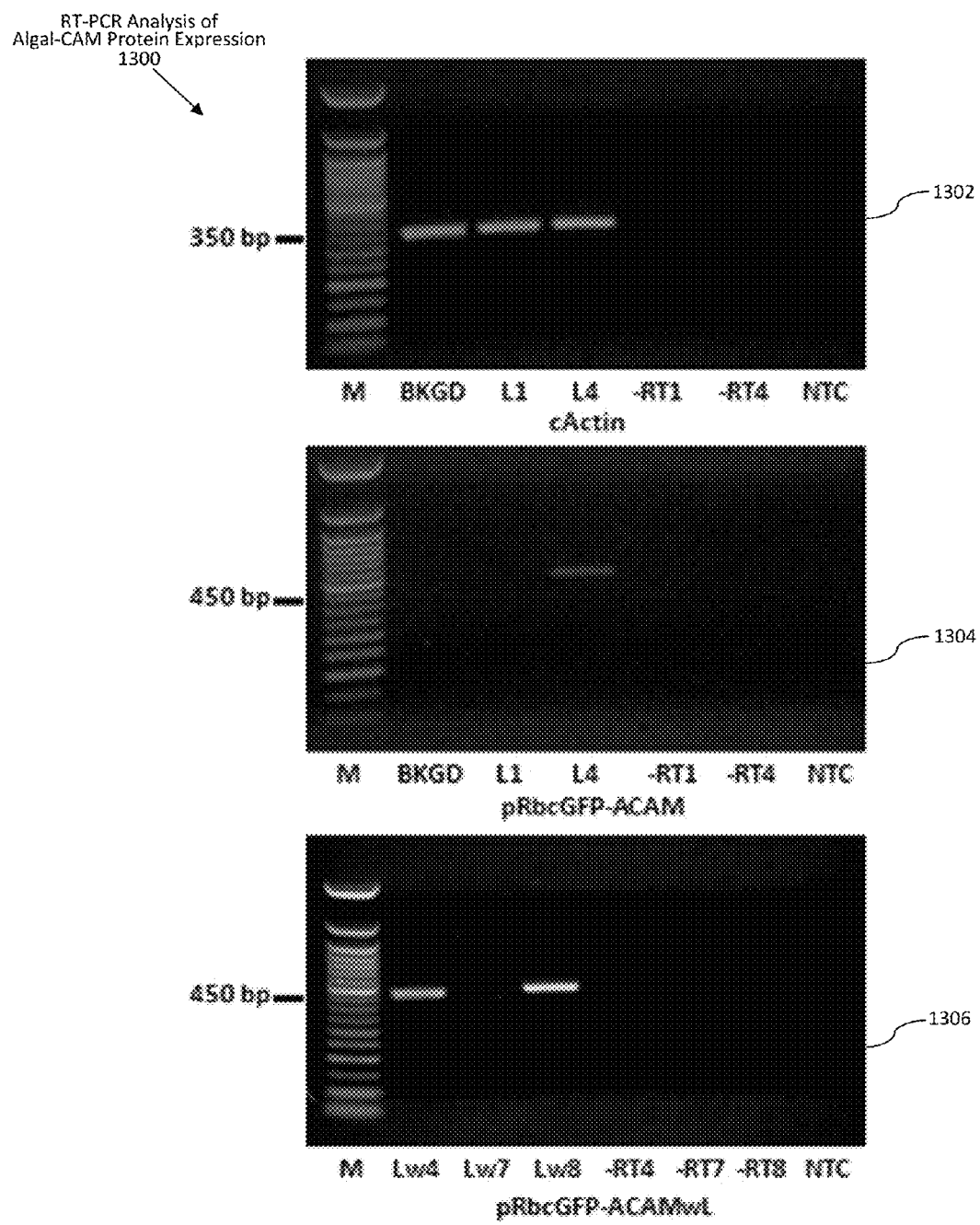
FIG. 13 is three photographs showing the results of three reverse transcription gel ("RT-PCR") transcript analyses showing transgene mRNA expression of the Algal-CAM protein.

FIG. 13 shows three photographs showing three RT-PCR gel analyses showing confirmed expression of the Algal-CAM protein 1300 in three strains of *C. reinhardtii*, labeled as L4, Lw4 and Lw8. In the first photograph, 1302 a control for both non-transformed and transformed *C. reinhardtii* is established where primers amplify a 344 bp region of cDNA representing spliced *Chlamydomonas* actin mRNA. In the middle 1304 and bottom photographs, 1306, primers amplify a 453 bp region of the transgene pRbcGFP-ACAM 1304 and pRbcGFP-ACAMwL cDNA 1306. The lanes in the three gels 1302, 1304 and 1306 are labeled with the first lane label M for the marker; BKGD indicates the non-transformed *C. reinhardtii* Δ Arg7 cw15 background strain and strains L1 and L4 1304 indicate transgenic strains with the Algal-CAM gene (pRbcGFP-ACAM transformants); Lw4, Lw7, and Lw8 1306 indicate transgenic strains for the Algal-CAM gene (pRbcGFP-ACAMwL transformants); −RT1, −RT4, −RT7 and −RT8 indicate Minus reverse transcriptase controls for strains L1, L4, Lw4, Lw7 and Lw8 RNA preparations (−RT4 for pRbcGFP-ACAMwL reefers to the −RT control for the Lw4 RNA preparation). As show in the middle photograph 1304 and bottom photograph 1306, the analysis confirmed expression of the Algal-CAM protein in the L4 transgenic strain 1304, as well as in the Lw4 and Lw8 1306 transgenic strains.

Figure 14:
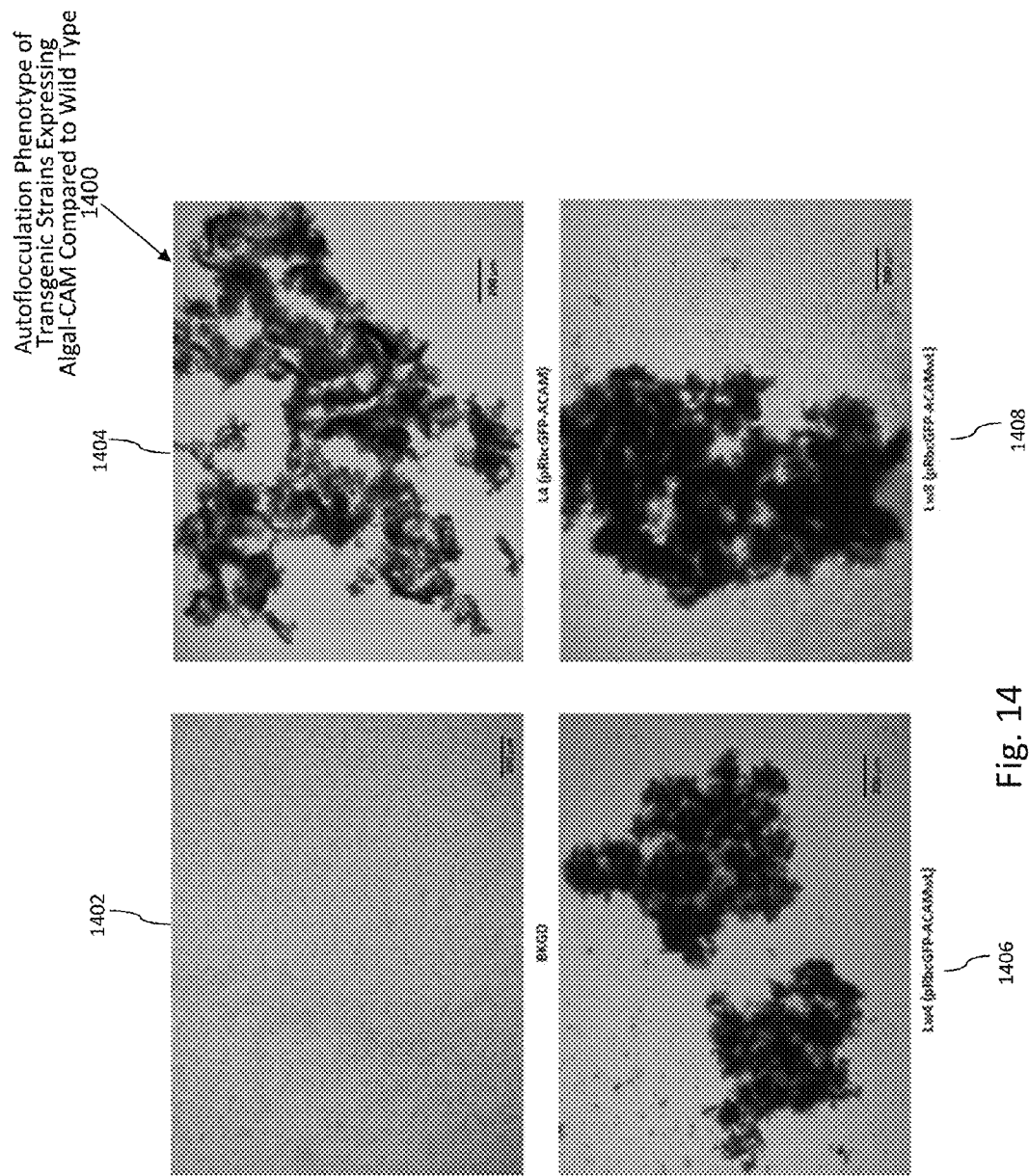
FIG. 14 is four micrographs showing a comparison of four unicellular cultures, one without the Algal-CAM protein and three cultures that were successfully transformed to express the Algal-CAM protein.

As shown in FIG. 14, autoflocculation phenotype of transgenic strains expressing Algal-CAM compared to wild type 1400 is further shown in four micrographs showing the flocculation or non-flocculation of four transgenic strains, BKGD 1402, L4 1404, Lw4 1406 and Lw8 1408 growing in four growth plates. BKGD 1402 indicates the non-transformed *C. reinhardtii* Δ Arg7 cw15 background strain; L4 1404 indicates a transformed transgenic strain with confirmed expression of the Algal-CAM gene (pRbcGFP-ACAM transformants); Lw4 1406 and Lw8 1408 indicate transformed transgenic strains for the confirmed expression of the Algal-CAM gene (pRbcGFP-ACAMwL transformants). The four cultures were incubated for 24 hours and photographed with an inverted microscope in the culture wells using a 2.5× objective. Micrographs were taken after lightly swirling the plates to separate and isolate individual flocculations. As shown in the photographs, BKGD 1402 does not show any coagulation or flocculation of organisms. L4 1404 acts more as a loose coagulation of smaller flocculation clumps while Lw4 1406 (third from the left) and Lw8 1408 act as a more cohesive large flocculation clumps. Please note the slight morphological difference in the Lw4 and Lw8 strains that contain a flexible amino acid linker separating the fusion domains compared to L4, which does not have a the flexible linker. Flocculations range from 800 µm to 1,700 µm in diameter as measured from these micrographs. Note how individual flocs adhere together to form large clumps.

Figure 15:
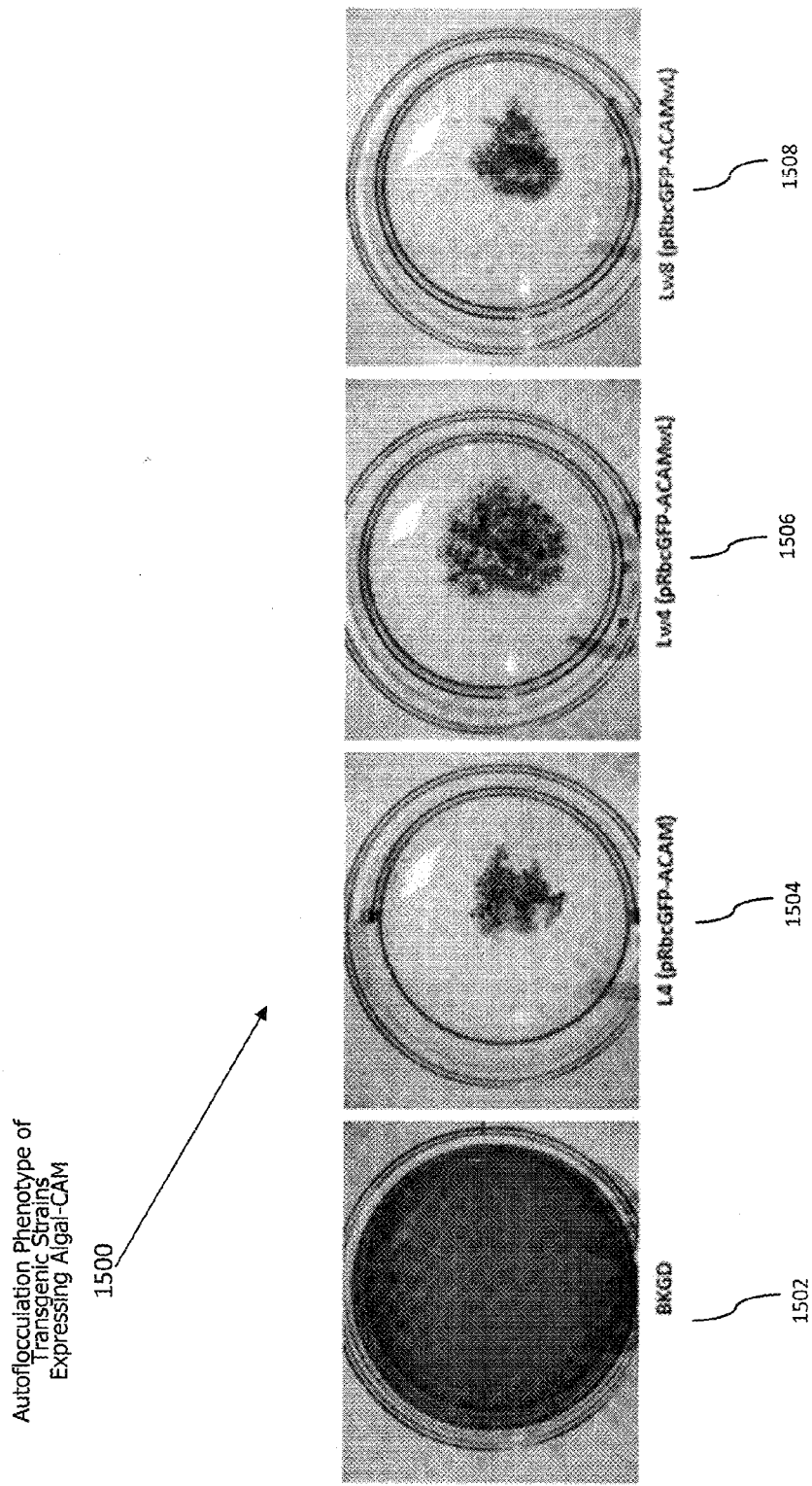
FIG. 15 is four photographs showing a comparison of four unicellular cultures, one without the Algal-CAM protein and three cultures which were successfully transformed to express the Algal-CAM protein.

As shown in FIG. 15, autoflocculation phenotype of transgenic strains expressing Algal-CAM 1500 in three strains of *C. reinhardtii* is shown in four photographs showing the flocculation or non-flocculation of four transgenic strains, BKGD 1502, L4 1504, Lw4 1506 and Lw8 1508 growing in four growth plates. Strain BKGD 1502 indicates the non-transformed *C. reinhardtii* Δ Arg7 cw15 background strain; strain L4 1504 indicates a transformed transgenic strain with confirmed to express the Algal-CAM gene (pRbcGFP-ACAM transformants); strains Lw4 1506 and Lw8 1508 indicate transformed transgenic strains confirmed to express the Algal-CAM gene (pRbcGFP-ACAMwL transformants). The four cultures were incubated for 24 hours and photographed using a high resolution camera. Photographs were taken of cells growing in 12 well culture plates. Culture wells are 2.0 cm in diameter. Photographs were taken after lightly swirling the plates to separate and isolate individual flocculations. As shown in the photographs, BKGD does not show as coagulation or flocculation, L4 1504 acts more as a loose coagulation of smaller flocculations while Lw4 1506 (third from the left) and Lw8 1508 act as a more cohesive large flocculations.

Example 2

Method of Producing *Chlamydomonas* Photosynthetic Unicells with the ISG, V1 or V2 Proteins

*Chlamydomonas* expression vectors are constructed using established recombinant DNA methods. ISG (SEQ ID NO:8), V1 (SEQ ID NO:4), and V2 (SEQ ID NO:6) transgenes from *Volvox* (UTEX #1886) are isolated by RT-PCR and cloned. For constitutive and/or inducible expression, a HSP70A/ RBCS2 promoter (SEQ ID NO:9), or a PSAD (SEQ ID NO:10), or both in tandem are used. A PCR is conducted and for advanced expression control, the thiamine-sensitive 5' riboswitch THI4 (SEQ ID NO:13) is used for translational regulation, and the NIT1 NO3-sensitive promoter for transcriptional regulation, or both in tandem for dual regulation. Transgenes include the ISG, VI or V2. *Volvox* cell wall genes already carry a native signal peptide that is highly conserved in volvocine green algae and functions in *Chlamydomonas* but a synthetic C-terminal FLAG tag/epitope is added to *Volvox* transgenes for immunolabeling. For *Chlamydomonas* transformation, the glass bead method is used, which places transgenes in the cell nucleus. Co-transformation with pArg7 selectable marker is used when transgenes are introduced in tandem on a single expression vector and transformants are selected for their ability to grow on arginine-free medium. The aphVIII resistance marker and selection for paromomycin resistance (SEQ ID NO:11 or SEQ ID NO:12) are used for vectors carrying a single transgene. Transgene presence and transcriptional expression in putative transformants is confirmed by PCR and RT-PCR, respectively. Protein expression levels and localization is observed by immunoblots directed against the C-terminal tags added to *Volvox* transgenes or the antigenic epitopes of human transgenes. Localization of heterologous proteins to the cell wall is confirmed with immunoblots of cell fractions.

Three *Chlamydomonas* strains are used. Wild type cells mate efficiently and have a cell wall composed of seven layers. These layers inhibit transformation but transformable protoplasts can be generated by enzymatic digestion of the cell wall. Cell wall layers 2, 4, and 6 form especially small mesh sizes and could prevent heterologous proteins from reaching the cell wall surface, which will be necessary for cell adhesion. The *Chlamydomonas* cw-15 mutant lacks cell wall layers 2, 4, and 6. It is easily transformed and its reduced cell wall allows heterologous cell wall proteins to reach the cell wall surface. A third *Chlamydomonas* line that is useful is the cw-ts1 strain, a temperature sensitive mutant capable of assembling a cell wall at 25° C. but not at 35° C. This mutant can be transformed at 35° C., when only a minimal cell wall is present, and then allowed to form a cell wall at 25° C. with inclusion of heterologous cell wall proteins. Combination of multiple transgenes can be achieved using the tandem expression vector pSI105 and pArg7 co-transformation.

For culturing of *Chlamydomonas* in 12 well plates for observation of cell-cell adhesion, 100 μl of 72 hr liquid culture is used to inoculate 3 ml of medium in 12 well culture plates grown for 24 hours in the light with shaking. Low magnification micrographs are then taken in the 12 well plates using an inverted Leica DMI3000 B microscope with a 2.5× objective after separating individual flocs by gentle rotary agitation. Higher magnification fluorescence micrographs are taken using a Zeiss 710 scanning confocal laser microscope at 63× magnification, 488 nm excitation, and 510 nm emission.

For culturing *Chlamydomonas* in 50 ml tubes for observation of cell-cell adhesion, 300 ul of 72 hr liquid culture is used to inoculate 5 ml of medium in 50 ml culture tubes that are grown for 72 hours under light with shaking. Cultures are vortexed and photographed. Cultures were then left to settle for 10 minutes and photographed again.

The expression of ISG, V1, or V2, in *Chlamydomonas*, singly or in combination, causes cell-cell adhesion and simple multicellularity. Cultures are rotated at 150 rpm on a 2.54 cm diameter of rotation in 125 ml culture flasks with baffles that increase shearing forces in the culture. Clump size is measured using Image J micrograph particle analysis software. Larger clump size is taken to indicate greater clump strength. For lines with inducible expression that causes cell-cell adhesion, sheets of cells are formed for analysis. Cells are filtered to a standard thickness of 100 μm on a 0.22 μm nitrocellulose filter and the filter placed on agar medium under inducing conditions. When cell adhesion is complete, the sheets of cells will be peeled off the filter for further study.

Example 3

Expression of Cadherin Protein

Example 2 is repeated with the exception that cadherin protein is used as a transgene. *Chlamydomonas* expression vectors are constructed using established recombinant DNA methods and the cell wall of the organism is removed using by means of induced mutation, fusing an enzyme to the organism or the construct that will degrade the cell wall. Cadherin protein gene sequences are then isolated from mammalian or algal genomic RT-PCRs and cloned. For constitutive and/or inducible expression, a Hsp70A/RbcS2 promoter (SEQ ID NO:9), a PSAD (SEQ ID NO:10) or other appropriate promoters are used. The cadherin gene sequence is operably linked to an algae specific transit peptide for transcription directed to the outer membrane or extracellular matrix of the algae. Further, the cadherin gene fuses to the C-terminus of a catenin protein. The fusion domains between the cadherin protein and the catenin protein act to bind the cadherin to actin filaments of the cytoskeleton, which will cause flocculation or cell adhesion of the algae. The N-terminal domains of the cadherin protein is hemophilic and binds with the same adhesion scheme of Algal-CAM in that the cadherin protein is homophilic and thus binds to itself. For advanced expression control, the thiamine-sensitive 5' riboswitch THI4 (SEQ ID NO:13) is used for translational regulation, and the NIT1 NO3-sensitive promoter for transcriptional regulation, or both in tandem for dual regulation. Transgenes will include the cadherin transgenes. For the quantification of the cell adhesion the quantification steps of Example 2 will be repeated.

Example 4

Expression of Claudin Protein

Example 2 is repeated with the exception that transmembrane claudin protein gene sequences are used as a transgene. *Chlamydomonas* expression vectors are constructed using established recombinant DNA methods and the cell wall of the organism is removed by means of induced mutation, fusing an enzyme to the organism or the construct that will degrade the cell wall. Claudin proteins are isolated from mammalian or algal DNA by RT-PCRs and cloned. For constitutive and/or inducible expression, a RbcS2/Hsp70A promoter (SEQ ID NO:9), PSAD promoter (SEQ ID NO:10) or other appropriate promoter is used. An algae specific transit peptide, for transcription directed to the outer membrane or extracellular matrix of the algae is included in the construct. For advanced expression control, the thiamine-sensitive 5' riboswitch THI4 (SEQ ID NO:13) is used for translational regulation, and the NIT1 NO3-sensitive promoter for transcriptional regulation, or both in tandem for dual regulation. Transgenes will include the claudin transgenes. For the quantification of the claudin cell adhesion the quantification steps of Example 2 will be repeated.

Example 5

Use of Selectable Marker to Quantify Cell Adhesion

Example 2 is repeated with the exception that a selectable marker is incorporated into the construct. *Chlamydomonas* expression vectors are constructed using established recombinant DNA methods. A selectable marker such as a paromomycin resistance marker (SEQ ID NO:11 and SEQ ID NO:12) is used. For the quantification of the cell adhesion proteins with a selectable marker, aminoglycoside antibiotic paromomycin is added to a bioreactor with the unicellular photosynthetic organisms. The paromycin will kill any unicells that do not contain the paromomycin resistance marker. Therefore, any unicells that are not killed will also contain the new construct with the resistance marker.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

---

We claim:

1. A transgenic unicellular photosynthetic organism chosen from *Chlamydomonas* spp, and *Dunaliella* spp., having a DNA construct stably integrated into the unicellular photosynthetic organism's genome under conditions suitable for expression of said DNA construct in an extracellular matrix, cell wall, plasma membrane or outer membrane of said unicellular photosynthetic organism, wherein said DNA construct comprises a promoter, wherein said promoter is operably linked to a cell adhesion protein coding sequence, wherein said cell adhesion protein coding sequence is chosen from an Algal-CAM protein, an ISG protein, a V1 protein, a V2 protein, a cadherin protein and a claudin protein wherein said cell adhesion protein coding sequence is expressed as a heterologous protein in the extracellular matrix, cell wall, plasma membrane or outer membrane of the organism, and wherein the expressed cell adhesion protein induces the unicellular photosynthetic organism to flocculate by adhering to one or more unicellular photosynthetic organisms.

2. The transgenic unicellular photosynthetic organism of claim 1, wherein said cell adhesion protein coding sequence of said DNA construct is chosen from SEQ ID NO:1, SEQ ID NO:3, SEQ ID NO:5, and SEQ ID NO:7.

3. The transgenic unicellular photosynthetic organism of claim 2, wherein said cell adhesion protein coding sequence of said DNA construct further comprises said cell adhesion protein coding sequence operably linked to a downstream regulatory region coding sequence.

4. The transgenic unicellular photosynthetic organism of claim 3, wherein said cell adhesion protein coding sequence of said DNA construct further comprises a translation regulator coding sequence operably linked to said promoter.

5. The transgenic unicellular photosynthetic organism of claim 1, wherein said cell adhesion protein coding sequence of said DNA construct further comprises a selectable marker coding sequence operably linked to said promoter coding sequence.

6. The transgenic unicellular photosynthetic organism of claim 5, wherein said selectable marker coding sequence of said DNA construct further comprises a reporter protein coding sequence operably linked to said cell adhesion protein coding sequence.

7. The transgenic unicellular photosynthetic organism of claim 1, further comprising a transit peptide sequence specific to the transgenic unicellular photosynthetic organism, wherein said transit peptide sequence is operably linked to said cell adhesion protein coding sequence, wherein said transit peptide sequence causes expression of the cell adhesion protein coding sequence in the extracellular matrix, cell wall, plasma membrane or outer membrane of the organism, and wherein the expressed cell adhesion protein induces the unicellular photosynthetic organism to flocculate by adhering to one or more unicellular photosynthetic organisms.

8. The transgenic unicellular photosynthetic organism of claim 1, wherein said cell adhesion protein coding sequence is an amino acid sequence chosen from SEQ ID NO:2, SEQ ID NO:4, SEQ ID NO:6, and SEQ ID NO:8.

* * * * *

SEQUENCE LISTING

```
<160> NUMBER OF SEQ ID NOS: 27

<210> SEQ ID NO 1
<211> LENGTH: 1406
<212> TYPE: DNA
<213> ORGANISM: Volvox carteri

<400> SEQUENCE: 1
ataattgctg gaaatgagag cccccagcat caacttacag gccttatttt aaaagacaca       60
gtattggatt ccaacagaga actatgcgga tggcaatcgc tgccttcatg aactaccttc      120
```

```
tcgcgtgcgc aggtctgctt cttttcctta cgcctgcatg gaaaagcaat gttcttgctt      180
ttacgtatcc gcctctgata gcctcgccgt cgtccttcac atcgcctccg ttaccatcta      240
cgccatcacc tccaccacca ctactgccgg ccctagcaag tcctcctccg ccgccgccta      300
acgaggatgt cgaccggccg cccctggtta aggacaacac gccaacaagt cccgcatcca      360
gccagccggc aataccacct ccctcgccgc accgtctacc cctcccaccc ctcctgtca       420 gctactcttc catctgggat tccttgtca agaacaacag cttcccaacg atcagtcttg        480
ccttgtcgac cgcaaatgaa gtcgcaacct tcaacgactc cagccaggag gtgaccttct      540
tcctgcccac tgagacggct tttgacaagt tgtcggacgc gctgggcgtt gccaggagca      600
accgtgcggg tttgttgccg tacttgccgg ttatcaaaag agccctaagc tatcacgtgc      660
taccgaccag aattagcctt cagagtgttg cgaatcaatc agtcggcggt acggagtact      720
acaacaccac gcttacgatg ggacagtcct caagcatcgg cgtgcgggtt cgcctccct       780 cgagcccccc ggcgacatcc ccggagatat tcattctggg ggttagctca accgctaaag      840
tactgcaggc tgatgtcgcg gcaggcgcgt cgtgcattaa tgtcgtggat accgttttgc      900
agtattggta caactcagtt gatgaggtct tcgcctccat cagcggcgcc tcgaccatgt      960
accaggcgct caagaccgcc caacttctca agccagcgaa tgtgacgagc ccgtacacca     1020
tattcgtacc aaccgacgag gccttcgtca gcgccttcgg tgcctccgcc gctaccacca     1080
tcctcgccaa tctaaggtcg tacgaaagct tgctacgtca ccatgtggca tacggctggg     1140
tggttacgga cacaacctca gaagaatacg ttcgtacatc gtacataact ctgaattcga     1200
acaacgtgac ggttgtggtt ccatcgaacg acaaggccga tgctggcgtc aagcccaccg     1260
tcgcctcagc tgccgtaccc ggatccccag tcttctccat cctaaataca ttccaagtcg     1320
gcatcgagcc acaagtgatc gtccaagtga ttaatggggt tcttaacccg gctagcagtc     1380
ggcagacagc cggtggcgca gcgtga                                           1406
```

<210> SEQ ID NO 2
<211> LENGTH: 440
<212> TYPE: PRT
<213> ORGANISM: Volvox carteri

<400> SEQUENCE: 2

```
Met Arg Met Ala Ile Ala Ala Phe Met Asn Tyr Leu Leu Ala Cys Ala
1               5                   10                  15

Gly Leu Leu Leu Phe Leu Thr Pro Ala Trp Lys Ser Asn Val Leu Ala
                20                  25                  30

Phe Thr Tyr Pro Pro Leu Ile Ala Ser Pro Ser Ser Phe Thr Ser Pro
            35                  40                  45

Pro Leu Pro Ser Thr Pro Ser Pro Pro Pro Leu Leu Pro Ala Leu
        50                  55                  60

Ala Ser Pro Pro Pro Pro Pro Asn Glu Asp Val Asp Arg Pro Pro
65                  70                  75                  80

Leu Val Lys Asp Asn Thr Pro Thr Ser Pro Ala Ser Ser Gln Pro Ala
                85                  90                  95

Ile Pro Pro Pro Ser Pro Pro Ser Thr Pro Thr Pro Pro Val
            100                 105                 110

Ser Tyr Ser Ser Ile Trp Asp Phe Leu Val Lys Asn Asn Ser Phe Pro
        115                 120                 125

Thr Ile Ser Leu Ala Leu Ser Thr Ala Asn Glu Val Ala Thr Phe Asn
    130                 135                 140
```

```
Asp Ser Ser Gln Glu Val Thr Phe Phe Leu Pro Thr Glu Thr Ala Phe
145                 150                 155                 160

Asp Lys Leu Ser Asp Ala Leu Gly Val Ala Arg Ser Asn Arg Ala Gly
                165                 170                 175

Leu Leu Pro Tyr Leu Pro Val Ile Lys Arg Ala Leu Ser Tyr His Val
            180                 185                 190

Leu Pro Thr Arg Ile Ser Leu Gln Ser Val Ala Asn Gln Ser Val Gly
        195                 200                 205

Gly Thr Glu Tyr Tyr Asn Thr Thr Leu Thr Met Gly Gln Ser Ser Ser
    210                 215                 220

Ile Gly Val Arg Val Ser Pro Pro Ser Ser Pro Ala Thr Ser Pro
225                 230                 235                 240

Glu Ile Phe Ile Leu Gly Val Ser Ser Thr Ala Lys Val Leu Gln Ala
                245                 250                 255

Asp Val Ala Ala Gly Ala Ser Cys Ile Asn Val Val Asp Thr Val Leu
                260                 265                 270

Gln Tyr Trp Tyr Asn Ser Val Asp Glu Val Phe Ala Ser Ile Ser Gly
            275                 280                 285

Ala Ser Thr Met Tyr Gln Ala Leu Lys Thr Ala Gln Leu Leu Lys Pro
290                 295                 300

Ala Asn Val Thr Ser Pro Tyr Thr Ile Phe Val Pro Thr Asp Glu Ala
305                 310                 315                 320

Phe Val Ser Ala Phe Gly Ala Ser Ala Ala Thr Thr Ile Leu Ala Asn
                325                 330                 335

Leu Arg Ser Tyr Glu Ser Leu Leu Arg His His Val Ala Tyr Gly Trp
            340                 345                 350

Val Val Thr Asp Thr Thr Ser Glu Glu Tyr Val Arg Thr Ser Tyr Ile
        355                 360                 365

Thr Leu Asn Ser Asn Asn Val Thr Val Val Pro Ser Asn Asp Lys
    370                 375                 380

Ala Asp Ala Gly Val Lys Pro Thr Val Ala Ser Ala Val Pro Gly
385                 390                 395                 400

Ser Pro Val Phe Ser Ile Leu Asn Thr Phe Gln Val Gly Ile Glu Pro
                405                 410                 415

Gln Val Ile Val Gln Val Ile Asn Gly Val Leu Asn Pro Ala Ser Ser
            420                 425                 430

Arg Gln Thr Ala Gly Gly Ala Ala
        435                 440

<210> SEQ ID NO 3
<211> LENGTH: 1773
<212> TYPE: DNA
<213> ORGANISM: Volvox carteri f. nagariensis

<400> SEQUENCE: 3
atggcgaaga caagtaatat gtggaatgct gttgcggcag ctttggcgct gacgtgggtt      60
gctatcgcag tcgcgcaata tgacgaggac ttcacggtct accgggatca aacaggggcc     120
ttcccgaact ttccctttcg taattgtgaa accacaaacg gggcatacca actggcacct     180
gtgtggcaac atgtgggcag caacaagtac tgctttagaa tccaggttcg ggaccctagc     240
tcctgcacgg gagcctgctg caacaccgac atgtacaaga tagagttcaa cgtgtccagc     300
agctgcctgg tggccggggc ttcagtcgtt gccaccgtga acggagcacc cactcgggtt     360
ggtgcgtcct tcgacaagcc cccgaccggc ccacctggct ccgccattct gcggctcacc     420
```

```
cagctggggc ttgacaccac gaccgcccag aatgcggagg tgtgcatcac cctcaggacc    480
aaccgcggag gccagggctg caccaccctg gagcaactgt gctcgtcacc gggcttttct    540
gcaggcacct gtacggcagc gatgtatgac acggcatgtg attgctgccc cacctctaga    600
gcctcgaagt attcccacc acctccaccg cctccaccat ctccatcgcc tccaccatct    660
ccaccgcctc caccatctcc accgcctcca ccacctccac cgcctccacc atctccaccg    720
cctccaccac ctccaccgcc tccaccttct ccaccgcctc caccatctcc accgcctcca    780
tctccaccac tgccgccgcc gtcaatcccc tctcctcctt tcgcattcgg attccggcca    840
ttttgcgatg tctgcatcaa ggcacagctg ctggctcctt tccccgatgt ccgacccttc    900
cgctacagca gcacaatgtg ctctgcaatc agcagaaga tcgctgacag catcaacgcc    960
ttggagcaag atccaaacct tggcttcgtc tataggattc catttgcacc gaatgacact   1020
cgctgcacag aaacccaggc tgttgtgtgt ggctcccttt atcagccagt taatgacaca   1080
gacgctttca agagaagct ctctcgctcc gtgagcgacc aggtgctgtt ctggctcgac    1140
gcggctacgg gggccgccag catttgcagc ccggaacttg acgggtacca agtgaccatt   1200
gagatcaccg tgatgattc aaatgggggc agctgcgtgc aagacagcag gtccatcgcc   1260
tgcactttgc caccagtccc atatcccaac tgcacgtgtg acatgcggca gggcgttatg   1320
ccatttgtgg tgggtacgcg ctacttcgcg cagcccagct ttaaagctga tttcggcacc   1380
accgagtact gcttccctat gagcattttc ccactgagcc agcttgtacc gagcacctgt   1440
aagggtgttg acatcctcaa gaagattgag tggtatgcga atgaggttct cagatcgtat   1500
gtcaagggtt tcaccctcta ccctagggtt ggtagtccac ggtcgatcgc gtccagctgg   1560
ggtgctgccg ggagctatac gctcaaagct accaacatta actggaatac cacgcaagcc   1620
gatggcgcca gatttgtgt ggttgtaaag aatccggtga ccatggcaga gctctgtcta   1680
ggcgcgtttg aagccaatg tttcgccacg ccatttaatg acgacaagga ctgctgcccc   1740
atgttccgta cggcgccgct gggaggccca taa                              1773
```

<210> SEQ ID NO 4
<211> LENGTH: 590
<212> TYPE: PRT
<213> ORGANISM: Volvox carteri f. nagariensis

<400> SEQUENCE: 4

```
Met Ala Lys Thr Ser Asn Met Trp Asn Ala Val Ala Ala Leu Ala
1               5                   10                  15

Leu Thr Trp Val Ala Ile Ala Val Ala Gln Tyr Asp Glu Asp Phe Thr
            20                  25                  30

Val Tyr Arg Asp Gln Thr Gly Ala Phe Pro Asn Phe Pro Phe Arg Asn
        35                  40                  45

Cys Glu Thr Thr Asn Gly Ala Tyr Gln Leu Ala Pro Val Trp Gln His
    50                  55                  60

Val Gly Ser Asn Lys Tyr Cys Phe Arg Ile Gln Val Arg Asp Pro Ser
65                  70                  75                  80

Ser Cys Thr Gly Ala Cys Cys Asn Thr Asp Met Tyr Lys Ile Glu Phe
                85                  90                  95

Asn Val Ser Ser Cys Leu Val Ala Gly Ala Ser Val Val Ala Thr
                100                 105                 110

Val Asn Gly Ala Pro Thr Arg Val Gly Ala Ser Phe Asp Lys Pro Pro
        115                 120                 125

Thr Gly Pro Pro Gly Ser Ala Ile Leu Arg Leu Thr Gln Leu Gly Leu
```

-continued

```
           130                 135                 140
Asp Thr Thr Thr Ala Gln Asn Ala Glu Val Cys Ile Thr Leu Arg Thr
145                 150                 155                 160

Asn Arg Gly Gly Gln Gly Cys Thr Thr Leu Glu Gln Leu Cys Ser Ser
                165                 170                 175

Pro Gly Phe Ser Ala Gly Thr Cys Thr Ala Ala Met Tyr Asp Thr Ala
                180                 185                 190

Cys Asp Cys Cys Pro Thr Ser Arg Ala Ser Lys Tyr Tyr Pro Pro Pro
                195                 200                 205

Pro Pro Pro Pro Pro Ser Pro Ser Pro Pro Ser Pro Pro Pro Pro
210                 215                 220

Pro Ser Pro Pro Pro Pro Pro Pro Pro Pro Pro Ser Pro Pro
225                 230                 235                 240

Pro Pro Pro Pro Pro Pro Pro Pro Ser Pro Pro Pro Pro Ser
                245                 250                 255

Pro Pro Pro Pro Ser Pro Pro Leu Pro Pro Pro Ser Ile Pro Ser Pro
                260                 265                 270

Pro Phe Ala Phe Gly Phe Arg Pro Phe Cys Asp Val Cys Ile Lys Ala
                275                 280                 285

Gln Leu Leu Ala Pro Phe Pro Asp Val Arg Pro Phe Arg Tyr Ser Ser
                290                 295                 300

Thr Met Cys Ser Ala Ile Gln Gln Lys Ile Ala Asp Ser Ile Asn Ala
305                 310                 315                 320

Leu Glu Gln Asp Pro Asn Leu Gly Phe Val Tyr Arg Ile Pro Phe Ala
                325                 330                 335

Pro Asn Asp Thr Arg Cys Thr Glu Thr Gln Ala Val Val Cys Gly Ser
                340                 345                 350

Leu Tyr Gln Pro Val Asn Asp Thr Asp Ala Phe Lys Glu Lys Leu Ser
                355                 360                 365

Arg Ser Val Ser Asp Gln Val Leu Phe Trp Leu Asp Ala Ala Thr Gly
370                 375                 380

Ala Ala Ser Ile Cys Ser Pro Glu Leu Asp Gly Tyr Gln Val Thr Ile
385                 390                 395                 400

Glu Ile Thr Gly Asp Asp Ser Asn Gly Gly Ser Cys Val Gln Asp Ser
                405                 410                 415

Arg Ser Ile Ala Cys Thr Leu Pro Pro Val Pro Tyr Pro Asn Cys Thr
                420                 425                 430

Cys Asp Met Arg Gln Gly Val Met Pro Phe Val Val Gly Thr Arg Tyr
                435                 440                 445

Phe Ala Gln Pro Ser Phe Lys Ala Asp Phe Gly Thr Thr Glu Tyr Cys
                450                 455                 460

Phe Pro Met Ser Ile Phe Pro Leu Ser Gln Leu Val Pro Ser Thr Cys
465                 470                 475                 480

Lys Gly Val Asp Ile Leu Lys Lys Ile Glu Trp Tyr Ala Asn Glu Val
                485                 490                 495

Leu Arg Ser Tyr Val Lys Gly Phe Thr Leu Tyr Pro Arg Val Gly Ser
                500                 505                 510

Pro Arg Ser Ile Ala Ser Ser Trp Gly Ala Ala Gly Ser Tyr Thr Leu
                515                 520                 525

Lys Ala Thr Asn Ile Asn Trp Asn Thr Thr Gln Ala Asp Gly Ala Lys
                530                 535                 540

Ile Cys Val Val Val Lys Asn Pro Val Thr Met Ala Glu Leu Cys Leu
545                 550                 555                 560
```

```
Gly Ala Phe Gly Ser Gln Cys Phe Ala Thr Pro Phe Asn Asp Asp Lys
                565                 570                 575

Asp Cys Cys Pro Met Phe Arg Thr Ala Pro Leu Gly Gly Pro
            580                 585                 590

<210> SEQ ID NO 5
<211> LENGTH: 1029
<212> TYPE: DNA
<213> ORGANISM: Volvox carteri f. nagariensis

<400> SEQUENCE: 5
atgaagctca ccaacgtcct gtgcattgct gtggctgtca gcctgctggc tggcgcccag      60
gccgcctcct tcccttacag ctcggtatgc gctcagcagc cggccgtcta ctccgtggag     120
tcgaccatca ttgagcgccc caacaacacc tactgcttta agatcgctgt caacgtgcct     180
gctaactgcg ctggctactg ctgctcggct gacctttaca gttcgagct  gagcatcaac     240
cctatctgca agattagcgg cgccaagctg agctctaccc tcaacggcaa gccaaccccc     300
acccagcctt ctatcgacaa gggcccc aac gagccggctg tgccatcct  gcgcattccg     360
aacctgggcc tcaagatgtc caacgccgat ggcgccgaga tttgcgtgag cctgggcacc     420
aactccgccg cagggggctg cctctcccctg gagcagctct gcaagccacc ggccggcggt     480
gctcccggca cctgcgagac tgccctgtgg gactccaagt tcaagtgctg cccaacggac     540
gttactgtgc ccaactctcc gcttctgccc cgcccccca  tcaactgcac gtgcgactac     600
aaggcaggtt ccacgccatt cactgttggc gccgccgcca  tgctacccc  caccacttcg     660
ggaaccaccg tgtactgcct gccgatcacc accacggaca  ccttcacccc agctggttgc     720
ggcccggtcg acatcctgca caagatcgag atgtacgcaa accaggatca gagggctgcg     780
attaagagcc tgaaactggt ctccggcagc accaccacga  ccctcgcggc tcctggaaac     840
ggcgctaaca gcaacactct gaagttcacc ccgatcaact ggaccaaggc tcaggccgcg     900
aactccaagg tctgcgtgga gctcaagaac ccaaccaccc tttcggactt ctgcctcggc     960
agcaagtgct acctcttcat cttcaacgcc aacagggcgt gctgcccgat gtacacggtt    1020
ccggtttaa                                                             1029

<210> SEQ ID NO 6
<211> LENGTH: 342
<212> TYPE: PRT
<213> ORGANISM: Volvox carteri f. nagariensis

<400> SEQUENCE: 6

Met Lys Leu Thr Asn Val Leu Cys Ile Ala Val Ala Val Ser Leu Leu
1               5                   10                  15

Ala Gly Ala Gln Ala Ala Ser Phe Pro Tyr Ser Ser Val Cys Ala Gln
            20                  25                  30

Gln Pro Ala Val Tyr Ser Val Glu Ser Thr Ile Ile Glu Arg Pro Asn
        35                  40                  45

Asn Thr Tyr Cys Phe Lys Ile Ala Val Asn Val Pro Ala Asn Cys Ala
    50                  55                  60

Gly Tyr Cys Cys Ser Ala Asp Leu Tyr Lys Phe Glu Leu Ser Ile Asn
65                  70                  75                  80

Pro Ile Cys Lys Ile Ser Gly Ala Lys Leu Ser Ser Thr Leu Asn Gly
                85                  90                  95

Lys Pro Thr Pro Thr Gln Pro Ser Ile Asp Lys Ala Pro Asn Glu Pro
            100                 105                 110
```

```
Ala Gly Ala Ile Leu Arg Ile Pro Asn Leu Gly Leu Lys Met Ser Asn
        115                 120                 125
Ala Asp Gly Ala Glu Ile Cys Val Ser Leu Gly Thr Asn Ser Ala Gly
    130                 135                 140
Arg Gly Cys Leu Ser Leu Glu Gln Leu Cys Lys Pro Pro Ala Gly Gly
145                 150                 155                 160
Ala Pro Gly Thr Cys Glu Thr Ala Leu Trp Asp Ser Lys Phe Lys Cys
                165                 170                 175
Cys Pro Thr Asp Val Thr Val Pro Asn Ser Pro Leu Leu Pro Pro Pro
                180                 185                 190
Pro Ile Asn Cys Thr Cys Asp Tyr Lys Ala Gly Ser Thr Pro Phe Thr
                195                 200                 205
Val Gly Ala Ala Thr Ala Thr Pro Thr Thr Ser Gly Thr Thr Val
    210                 215                 220
Tyr Cys Leu Pro Ile Thr Thr Thr Asp Thr Phe Thr Pro Ala Gly Cys
225                 230                 235                 240
Gly Pro Val Asp Ile Leu His Lys Ile Glu Met Tyr Ala Asn Gln Asp
                245                 250                 255
Gln Arg Ala Ala Ile Lys Ser Leu Lys Leu Val Ser Gly Ser Thr Thr
            260                 265                 270
Thr Thr Leu Ala Ala Ser Trp Asn Gly Ala Asn Ser Asn Thr Leu Lys
            275                 280                 285
Phe Thr Pro Ile Asn Trp Thr Lys Ala Gln Ala Ala Asn Ser Lys Val
        290                 295                 300
Cys Val Glu Leu Lys Asn Pro Thr Thr Leu Ser Asp Phe Cys Leu Gly
305                 310                 315                 320
Ser Lys Cys Tyr Leu Phe Ile Phe Asn Ala Asn Arg Ala Cys Cys Pro
                325                 330                 335
Met Tyr Thr Val Pro Val
            340

<210> SEQ ID NO 7
<211> LENGTH: 1099
<212> TYPE: DNA
<213> ORGANISM: Volvox carteri f. nagariensis

<400> SEQUENCE: 7
tgtgcctctg gaggctccct cttttgggg tccaggccac tgatactcat aagaggcagc      60
ggatccttct agccgaacgg tctgaaaaga tgggttcgcg tagcgtcgcc acgaccacgc    120
ggacgttcgg cttgttcgct gcggcatctc tactgctcgc gtgccaagct tccgctgctg    180
tttcatattc tgtaagcgtc tacaacaaca tcgcggtcac aggggctccc ctctctggca    240
tcgtgtctca gctgctatcc aaatggaagc tcaatgttcc cactttgagg acagtctact    300
cccagccgag cgctgcagag ttgtcaagca ccaacgcctt tatcgtatac tccaagggtc    360
agggctccta ctggattacg gaaggcctga cctcgaactc aactaaggtt aacgatctac    420
tcacatttgt ccgtaatgga ggttccctta tccttgtcaa cggcgccaac ggaaatgaca    480
acacatttat tcctcttatt cacgcgctga ctggcgggga tactctctgc atcgcgagga    540
gctacgcaga tgacactcgc atctaccgtc gcatcgaccc tccatccaac tttggcaacc    600
tgcctgtcaa gcagttccgc tacactgcga tctgtatat taccggccta gactgcttat    660
ctggcacctc tatttattcc tccgacccaa ccaaaaagct ttacgccatc tctgccggca    720
tcacatggag cgtgggacag ggcgccgtga cgtgggtcgg cgccgacatt gtggctgact    780
```

-continued

```
ccaagaacac cgtagccttg gtgacagctg cggcggtcgt cgtacagaca accccgtcgc      840
cgccgccgcc gccacgagtt tcaacgtcgc cgccgccacc agcccgtgtc tcatcctcgc      900
cgccgcccgc cacgcgctcg ccgccacccc gtcgtataac gtctccttca ccagtcctca      960
ctgcatcccc accactcccg aaaagatcgc caccaccgcc gccgcgcgtc ccgccctcgc     1020
cgccaccacc ggttgcttct ccgccgccac caccacctcc acgcgtctcc ccgtcgccgc     1080
ctccgccgca gccagtttc                                                   1099
```

<210> SEQ ID NO 8
<211> LENGTH: 336
<212> TYPE: PRT
<213> ORGANISM: Volvox carteri f. nagariensis

<400> SEQUENCE: 8

```
Met Gly Ser Arg Ser Val Ala Thr Thr Thr Arg Thr Phe Gly Leu Phe
1               5                   10                  15

Ala Ala Ala Ser Leu Leu Ala Cys Gln Ala Ser Ala Ala Val Ser
            20                  25                  30

Tyr Ser Val Ser Val Tyr Asn Asn Ile Ala Val Thr Gly Ala Pro Leu
        35                  40                  45

Ser Gly Ile Val Ser Gln Leu Ser Lys Trp Lys Leu Asn Val Pro
    50                  55                  60

Thr Leu Arg Thr Val Tyr Ser Gln Pro Ser Ala Ala Glu Leu Ser Ser
65                  70                  75                  80

Thr Asn Ala Phe Ile Val Tyr Ser Lys Gly Gln Gly Ser Tyr Trp Ile
                85                  90                  95

Thr Glu Gly Leu Thr Ser Asn Ser Thr Lys Val Asn Asp Leu Leu Thr
            100                 105                 110

Phe Val Arg Asn Gly Gly Ser Leu Ile Leu Val Asn Gly Ala Asn Gly
        115                 120                 125

Asn Asp Asn Thr Phe Ile Pro Leu Ile His Ala Leu Thr Gly Gly Asp
    130                 135                 140

Thr Leu Cys Ile Ala Arg Ser Tyr Ala Asp Asp Thr Arg Ile Tyr Arg
145                 150                 155                 160

Arg Ile Asp Pro Pro Ser Asn Phe Gly Asn Leu Pro Val Lys Gln Phe
                165                 170                 175

Arg Tyr Thr Ala Asp Leu Tyr Ile Thr Gly Leu Asp Cys Leu Ser Gly
            180                 185                 190

Thr Ser Ile Tyr Ser Ser Asp Pro Thr Lys Lys Leu Tyr Ala Ile Ser
        195                 200                 205

Ala Gly Ile Thr Trp Ser Val Gly Gln Gly Ala Val Thr Trp Val Gly
    210                 215                 220

Ala Asp Ile Val Ala Asp Ser Lys Asn Thr Val Ala Leu Val Thr Ala
225                 230                 235                 240

Ala Ala Val Val Val Gln Thr Thr Pro Ser Pro Pro Pro Pro Arg
                245                 250                 255

Val Ser Thr Ser Pro Pro Pro Ala Arg Val Ser Ser Pro Pro
            260                 265                 270

Pro Ala Thr Arg Ser Pro Pro Pro Arg Arg Ile Thr Ser Pro Ser Pro
        275                 280                 285

Val Leu Thr Ala Ser Pro Pro Leu Pro Lys Arg Ser Pro Pro Pro
    290                 295                 300

Pro Arg Val Pro Pro Ser Pro Pro Pro Val Ala Ser Pro Pro Pro
```

|  | 305 |  |  | 310 |  |  | 315 |  |  | 320 |  |
| --- | --- | --- | --- | --- | --- | --- | --- | --- | --- | --- | --- |
| Pro | Pro | Pro | Pro | Arg | Val | Ser | Pro | Ser | Pro | Pro | Pro |
|  |  |  | 325 |  |  |  |  | 330 |  |  |  |

|  | Gln | Pro | Val |
| --- | --- | --- | --- |
|  |  | 335 |  |

<210> SEQ ID NO 9
<211> LENGTH: 5298
<212> TYPE: DNA
<213> ORGANISM: Artificial sequence
<220> FEATURE:
<223> OTHER INFORMATION: Synthetic sequence

<400> SEQUENCE: 9

| ctgacgcgcc ctgtagcggc gcattaagcg cggcgggtgt ggtggttacg cgcagcgtga | 60 |
| --- | --- |
| ccgctacact tgccagcgcc ctagcgcccg ctcctttcgc tttcttccct tcctttctcg | 120 |
| ccacgttcgc cggcttgaca tgattggtgc gtatgtttgt atgaagctac aggactgatt | 180 |
| tggcgggcta tgagggcgcg ggaagctctg aagggccgc gatgggcgc gcggcgtcca | 240 |
| gaaggcgcca tacggcccgc tggcggcacc catccggtat aaaagcccgc gaccccgaac | 300 |
| ggtgacctcc actttcagcg acaaacgagc acttatacat acgcgactat tctgccgcta | 360 |
| tacataacca ctcagctagc ttaagatccc atcaagcttg catgccgggc gcgcagaag | 420 |
| gagcgcagcc aaaccaggat gatgtttgat ggggtatttg agcacttgca acccttatcc | 480 |
| ggaagcccc tggcccacaa aggctaggcg ccaatgcaag cagttcgcat gcagcccctg | 540 |
| gagcggtgcc ctcctgataa accggccagg gggcctatgt tctttacttt tttacaagag | 600 |
| aagtcactca acatcttaaa atggccaggt gagtcgacga gcaagcccgg cggatcaggc | 660 |
| agcgtgcttg cagatttgac ttgcaacgcc cgcattgtgt cgacgaaggc ttttggctcc | 720 |
| tctgtcgctg tctcaagcag catctaaccc tgcgtcgccg tttccatttg caggatggcc | 780 |
| actccgccct ccccggtgct gaagaatttc gaagcatgga cgatgcgttg cgtgcactgc | 840 |
| ggggtcggta tcccggttgt gagtgggttg ttgtggagga tggggcctcg ggggctggtg | 900 |
| tttatcggct tcgggtggt gggcgggagt tgtttgtcaa ggtggcagct ctgggggccg | 960 |
| gggtgggctt gttgggtgag gctgagcggc tggtgtggtt ggcggaggtg gggattcccg | 1020 |
| tacctcgtgt tgtggagggt ggtggggacg agagggtcgc ctggttggtc accgaagcgg | 1080 |
| ttccggggcg tccggccagt gcgcggtggc cgcgggagca gcggctggac gtggcggtgg | 1140 |
| cgctcgcggg gctcgctcgt tcgctgcacg cgctggactg ggagcggtgt ccgttcgatc | 1200 |
| gcagtctcgc ggtgacggtg ccgcaggcgg cccgtgctgt cgctgaaggg agcgtcgact | 1260 |
| tggaggatct ggacgaggag cggaaggggt ggtcggggga gcggcttctc gccgagctgg | 1320 |
| agcggactcg gcctgcggac gaggatctgg cggtttgcca cggtcacctg tgcccggaca | 1380 |
| acgtgctgct cgaccctcgt acctgcgagg tgaccgggct gatcgacgtg ggcgggtcg | 1440 |
| gccgtgcgga ccggcactcc gatctcgcgc tggtgctgcg cgagctggcc cacgaggagg | 1500 |
| acccgtggtt cgggccggag tgttccgcgg cgttcctgcg ggagtacggg cgcggtggg | 1560 |
| atggggcggt atcggaggaa aagctggcgt tttaccggct gttggacgag ttcttctgag | 1620 |
| ggacctgatg gtgttggtgg ctgggtaggg ttgcgtcgcg tgggtgacag cacagtgtgg | 1680 |
| acgttgggat ccccgctccg tgtaaatgga ggcgctcgtt gatctgagcc ttgccccctg | 1740 |
| acgaacggcg gtggatggaa gatactgctc tcaagtgctg aagcggtagc ttagctcccc | 1800 |
| gtttcgtgct gatcagtctt tttcaacacg taaaaagcgg aggagtttg caattttgtt | 1860 |
| ggttgtaacg atcctccgtt gattttggcc tctttctcca tgggcgggct gggcgtattt | 1920 |

```
gaagcgggta cccagctttt gttcccttta gtgagggtta attgcgcgct ggcgtaatc    1980
atggtcatag ctgttttcctg tgtgaaattg ttatccgctc acaattccac acaacatacg   2040
agccggaagt ctagacggcg gggagctcgc tgaggcttga catgattggt gcgtatgttt   2100
gtatgaagct acaggactga tttggcgggc tatgagggcg cgggaagctc tggaagggcc   2160
gcgatggggc gcgcggcgtc cagaaggcgc catacggccc gctggcggca cccatccggt   2220
ataaaagccc gcgaccccga acggtgacct ccactttcag cgacaaacga gcacttatac   2280
atacgcgact attctgccgc tatacataac cactcagcta gcttaagatc ccatcaagct   2340
tgcatgccgg gcgcgccaga aggagcgcag ccaaaccagg atgatgtttg atggggtatt   2400
tgagcacttg caacccttat ccggaagccc cctggcccac aaaggctagg cgccaatgca   2460
agcagttcgc atgcagcccc tggagcgtg ccctcctgat aaaccggcca gggggcctat   2520
gttctttact ttttttacaag agaagtcact caacatctta aaatggccag gtgagtcgac   2580
gagcaagccc ggcggatcag gcagcgtgct tgcagatttg acttgcaacg cccgcattgt   2640
gtcgacgaag gcttttggct cctctgtcgc tgtctcaagc agcatctaac cctgcgtcgc   2700
cgtttccatt tgcaggatgg ccactccgcc ctccccggtg ctgaagaatt tcgaaattaa   2760
ccctcactaa agggaacaaa agctgggtac cgggcccccc ctcgaggtcg acggtatcga   2820
taagcttgat atcgaattcc tgcagcccgg gggatccccg ctccgtgtaa atggaggcgc   2880
tcgttgatct gagccttgcc ccctgacgaa cggcggtgga tggaagatac tgctctcaag   2940
tgctgaagcg gtagcttagc tccccgtttc gtgctgatca gtcttttttca acacgtaaaa   3000
agcggaggag ttttgcaatt ttgttggttg taacgatcct ccgttgattt tggcctcttt   3060
ctccatgggc gggctgggcg tatttgaagc gggtacccag cttttgttcc ctttagtgag   3120
ggttaattgc gcgcttggcg taatcatggt catagctgtt tcctgtgtga aattgttatc   3180
cgctcacaat tccacacaac atacgagccg gaagcataaa gtgtaaagcc tggggtgcct   3240
aatgagtgag ctaactcaca ttaattgcgt tgcgctcact gcccgctttc cagtcgggaa   3300
acctgtcgtg ccagctgcat taatgaatcg gccaacgcgc ggggagaggc ggtttgcgta   3360
ttgggcgctc ttccgcttcc tcgctcactg actcgctgcg ctcggtcgtt cggctgcggc   3420
gagcggtatc agctcactca aaggcggtaa tacggttatc cacagaatca ggggataacg   3480
caggaaagaa catgtgagca aaaggccagc aaaaggccag gaaccgtaaa aaggccgcgt   3540
tgctggcgtt tttccatagg ctccgccccc ctgacgagca tcacaaaaat cgacgctcaa   3600
gtcagaggtg gcgaaacccg acaggactat aaagatacca ggcgtttccc cctggaagct   3660
ccctcgtgcg ctctcctgtt ccgaccctgc cgcttaccgg atacctgtcc gcctttctcc   3720
cttcgggaag cgtggcgctt tctcatagct cacgctgtag gtatctcagt tcggtgtagg   3780
tcgttcgctc caagctgggc tgtgtgcacg aaccccccgt tcagcccgac cgctgcgcct   3840
tatccggtaa ctatcgtctt gagtccaacc cggtaagaca cgacttatcg ccactggcag   3900
cagccactgg taacaggatt agcagagcga ggtatgtagg cggtgctaca gagttcttga   3960
agtggtggcc taactacggc tacactagaa ggacagtatt tggtatctgc gctctgctga   4020
agccagttac cttcggaaaa agagttggta gctcttgatc cggcaaacaa accaccgctg   4080
gtagcggtgg tttttttgtt tgcaagcagc agattacgcg cagaaaaaaa ggatctcaag   4140
aagatccttt gatcttttct acggggtctg acgctcagtg gaacgaaaac tcacgttaag   4200
ggattttggt catgagatta tcaaaaagga tcttcaccta gatcctttta aattaaaaat   4260
gaagttttaa atcaatctaa agtatatatg agtaaacttg gtctgacagt taccaatgct   4320
```

```
taatcagtga ggcacctatc tcagcgatct gtctatttcg ttcatcccata gttgcctgac    4380 tccccgtcgt gtagataact acgatacggg agggcttacc atctggcccc agtgctgcaa    4440
tgataccgcg agacccacgc tcaccggctc cagatttatc agcaataaac cagccagccg    4500
gaagggccga gcgcagaagt ggtcctgcaa ctttatccgc ctccatccag tctattaatt    4560
gttgccggga agctagagta agtagttcgc cagttaatag tttgcgcaac gttgttgcca    4620
ttgctacagg catcgtggtg tcacgctcgt cgtttggtat ggcttcattc agctccggtt    4680
cccaacgatc aaggcgagtt acatgatccc ccatgttgtg caaaaaagcg gttagctcct    4740
tcggtcctcc gatcgttgtc agaagtaagt tggccgcagt gttatcactc atggttatgg    4800
cagcactgca taattctctt actgtcatgc catccgtaag atgcttttct gtgactggtg    4860
agtactcaac caagtcattc tgagaatagt gtatgcggcg accgagttgc tcttgcccgg    4920
cgtcaatacg ggataatacc gcgccacata gcagaacttt aaaagtgctc atcattggaa    4980
aacgttcttc ggggcgaaaa ctctcaagga tcttaccgct gttgagatcc agttcgatgt    5040
aacccactcg tgcacccaac tgatcttcag catctttttac tttcaccagc gtttctgggt    5100
gagcaaaaac aggaaggcaa aatgccgcaa aaagggaat aagggcgaca cggaaatgtt    5160
gaatactcat actcttcctt tttcaatatt attgaagcat ttatcagggt tattgtctca    5220
tgagcggata catatttgaa tgtatttaga aaaataaaca aatagggggtt ccgcgcacat    5280 ttccccgaaa agtgccac                                                 5298

<210> SEQ ID NO 10
<211> LENGTH: 820
<212> TYPE: DNA
<213> ORGANISM: Chlamydomonas sp.

<400> SEQUENCE: 10
ggatcccaca cacctgcccg tctgcctgac aggaagtgaa cgcatgtcga gggaggcctc      60
accaatcgtc acacgagccc tcgtcagaaa cacgtctccg ccacgctctc cctctcacgg     120
ccgaccccgc agccctttg ccctttccta ggccaccgac aggacccagg cgctctcagc     180
atgcctcaac aacccgtact cgtgccagcg gtgcccttgt gctggtgatc gcttggaagc     240
gcatgcgaag acgaaggggc ggagcaggcg gcctggctgt tcgaagggct cgccgccagt     300
tcgggtgcct ttctccacgc gcgcctccac acctaccgat gcgtgaaggc aggcaaatgc     360
tcatgtttgc ccgaactcgg agtccttaaa aagccgcttc ttgtcgtcgt tccgagacat     420
gttagcagat cgcagtgcca cctttcctga cgcgctcggc cccatattcg gacgcaattg     480
tcatttgtag cacaattgga gcaaatctgg cgaggcagta ggcttttaag ttgcaaggcg     540
agagagcaaa gtgggacgcg gcgtgattat tggtatttac gcgacggccc ggcgcgttag     600
cggcccttcc cccaggccag ggacgattat gtatcaatat tgttgcgttc gggcactcgt     660
gcgagggctc ctgcggggctg gggaggggga tctgggaatt ggaggtacga ccagatggc      720 ttgctcgggg ggaggtttcc tcgccgagca agccagggtt aggtgttgcg ctcttgactc     780
gttgtgcatt ctaggacccc actgctactc acaacaagcc                           820

<210> SEQ ID NO 11
<211> LENGTH: 819
<212> TYPE: DNA
<213> ORGANISM: Streptomyces rimosus

<400> SEQUENCE: 11
```

```
atggacgatg cgttgcgtgc actgcggggt cggtatcccg gttgtgagtg ggttgttgtg      60
gaggatgggg cctcggggc tggtgtttat cggcttcggg gtggtgggcg ggagttgttt     120
gtcaaggtgg cagctctggg ggccggggtg ggcttgttgg gtgaggctga gcggctggtg     180
tggttggcgg aggtggggat tcccgtacct cgtgttgtgg agggtggtgg ggacgagagg     240
gtcgcctggt tggtcaccga agcggttccg gggcgtccgg ccagtgcgcg gtggccgcgg     300
gagcagcggc tggacgtggc ggtggcgctc gcggggctcg ctcgttcgct gcacgcgctg     360
gactgggagc ggtgtccgtt cgatcgcagt ctcgcggtga cggtgccgca gcggcccgt      420 gctgtcgctg aagggagcgt cgacttggag gatctggacg aggagcggaa ggggtggtcg     480
ggggagcggc ttctcgccga gctggagcgg actcggcctg cggacgagga tctggcggtt     540
tgccacggtg acctgtgccc ggacaacgtg ctgctcgacc ctcgtacctg cgaggtgacc     600
gggctgatcg acgtgggggcg gtcggccgt gcggaccggc actccgatct cgcgctggtg     660
ctgcgcgagc tggcccacga ggaggacccg tggttcgggc cggagtgttc cgcggcgttc     720
ctgcgggagt acgggcgcgg gtgggatggg gcggtatcgg aggaaaagct ggcgttttac     780
cggctgttgg acgagttctt ctgagggacc tgatggtgt                           819
```

<210> SEQ ID NO 12
<211> LENGTH: 1503
<212> TYPE: DNA
<213> ORGANISM: Streptomyces rimosus

<400> SEQUENCE: 12

```
ggcttgacat gattggtgcg tatgtttgta tgaagctaca ggactgattt ggcgggctat      60
gagggcgcgg gaagctctgg aagggccgcg atggggcgcg cggcgtccag aaggcgccat     120
acggcccgct ggcggcaccc atccggtata aaagcccgcg accccgaacg gtgacctcca     180
ctttcagcga caaacgagca cttatacata cgcgactatt ctgccgctat acataaccac     240
tcagctagct taagatccca tcaagcttgc atgccgggcg cgccagaagg agcgcagcca     300
aaccaggatg atgtttgatg gggtatttga gcacttgcaa cccttatccg gaagcccct     360 ggcccacaaa ggctaggcgc caatgcaagc agttcgcatg cagcccctgg agcggtgccc     420
tcctgataaa ccggccaggg ggcctatgtt ctttactttt ttacaagaga agtcactcaa     480
catcttaaaa tggccaggtg agtcgacgag caagcccggc ggatcaggca gcgtgcttgc     540
agatttgact tgcaacgccc gcattgtgtc gacgaaggct tttggctcct ctgtcgctgt     600
ctcaagcagc atctaaccct gcgtcgccgt ttccatttgc aggatggcca ctccgccctc     660
cccggtgctg aagaatttcg aagcatggac gatgcgttgc gtgcactgcg gggtcggtat     720
cccggttgtg agtgggttgt tgtggaggat ggggcctcgg gggctggtgt ttatcggctt     780
cggggtggtg ggcgggagtt gtttgtcaag gtggcagctc tggggggccgg ggtgggcttg     840 ttgggtgagg ctgagcggct ggtgtggttg gcggaggtgg ggattcccgt acctcgtgtt     900
gtggagggtg gtgggacga gagggtcgcc tggttggtca ccgaagcggt tccggggcgt     960
ccggccagtg cgcggtggcc gcgggagcag cggctggacg tggcggtggc gctcgcgggg    1020
ctcgctcgtt cgctgcacgc gctggactgg gagcggtgtc cgttcgatcg cagtctcgcg    1080
gtgacggtgc cgcaggcggc ccgtgctgtc gctgaaggga gcgtcgactt ggaggatctg    1140
gacgaggagc ggaaggggtg gtcggggag cggcttctcg ccgagctgga gcggactcgg    1200
cctgcggacg aggatctggc ggtttgccac ggtgacctgt gcccggacaa cgtgctgctc    1260
gaccctcgta cctgcgaggt gaccgggctg atcgacgtgg ggcgggtcgg ccgtgcggac    1320
```

```
cggcactccg atctcgcgct ggtgctgcgc gagctggccc acgaggagga cccgtggttc      1380
gggccggagt gttccgcggc gttcctgcgg gagtacgggc gcgggtggga tggggcggta      1440
tcggaggaaa agctggcgtt ttaccggctg ttggacgagt tcttctgagg gacctgatgg      1500
tgt                                                                   1503

<210> SEQ ID NO 13
<211> LENGTH: 274
<212> TYPE: DNA
<213> ORGANISM: Chlamydomonas sp.

<400> SEQUENCE: 13
gagctgtcgc atagatcgcc tttgcgctcg caactccccg ttgcttttga gccctcgccg        60
ccctctgcgc cctcctcgct gtaacgcaag actcgacatt gctaattggc atcggcttct       120
ctcgctctct ggcgacgact gctgcggcgc tggccttatc attcgggcat gtcactgacg       180
cccctcgcat cggcccgcgc ccgcgctgct cgcccgcccg cctcctcccc cctgcccctc       240
ctttctcaac cttccagaac cttcttcacc aaag                                   274

<210> SEQ ID NO 14
<211> LENGTH: 5808
<212> TYPE: DNA
<213> ORGANISM: Artificial Sequence
<220> FEATURE:
<223> OTHER INFORMATION: Synthetic Organism

<400> SEQUENCE: 14
ctgacgcgcc ctgtagcggc gcattaagcg cggcgggtgt ggtggttacg cgcagcgtga        60
ccgctacact tgccagcgcc ctagcgcccg ctcctttcgc tttcttccct tcctttctcg       120
ccacgttcgc cggctttccc cgtcaagctc taaatcgggg gctcccttta gggttccgat       180
ttagtgcttt acggcacctc gaccccaaaa aacttgatta gggtgatggt tcacgtagtg       240
ggccatcgcc ctgatagacg gtttttcgcc ctttgacgtt ggagtccacg ttctttaata       300
gtggactctt gttccaaact ggaacaacac tcaaccctat ctcggtctat tcttttgatt       360
tataagggat tttgccgatt tcggcctatt ggttaaaaaa tgagctgatt taacaaaaat       420
ttaacgcgaa ttttaacaaa atattaacgc ttacaatttc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta tagggcgaat tggagctcgc       660
tgaggcttga catgattggt gcgtatgttt gtatgaagct acaggactga tttggcgggc       720
tatgagggcg ggggaagctc tggaagggcc gcgatgggc gcgcggcgtc cagaaggcgc       780
catacggccc gctggcggca cccatccggt ataaaagccc gcgaccccga acggtgacct       840
ccactttcag cgacaaacga gcacttatac atacgcgact attctgccgc tatacataac       900
cactcagcta gcttaagatc ccatcaagct tgcattccgg gcgcgccaga aggagcgcag       960
ccaaaccagg atgatgtttg atgggtatt tgagcacttg caacccttat ccggaagccc      1020
cctggcccac aaaggctagg cgccaatgca agcagttcgc atgcagcccc tggagcggtg      1080
ccctcctgat aaaccggcca ggggccctat gttctttact tttttacaag agaagtcact      1140
caacatctta aaatgccag gtgagtcgac gagcaagccc ggcggatcag gcagcgtgct      1200
tgcagatttg acttgcaacg cccgcattgt gtcgacgaag gcttttggct cctctgtcgc      1260
```

```
tgtctcaagc agcatctaac cctgcgtcgc cgtttccatt tgcaggatgc tcgagggaag    1320
atctatgcgg atggcaatcg ctgccttcat gaactacctt ctcgcgtgcg caggtctgct    1380
tcttttcctt acgcctgcat ggaaaagcaa tgttcttgct tttacgtatc cgcctctgat    1440
agcctcgccg tcgtccttca catcgcctcc gttaccatct acgccatcac ctccaccacc    1500
actactgccg gccctagcaa gtcctcctcc gccgccgcct aacgaggatg tcgaccggcc    1560 gccccctggtt aaggacaaca cgccaacaag tcccgcatcc agccagccgg caataccacc    1620
tccctcgccg ccaccgtcta cccctcccac ccctcctgtc agctactctt ccatctggga    1680
tttccttgtc aagaacaaca gcttcccaac gatcagtctt gccttgtcga ccgcaaatga    1740
agtcgcaacc ttcaacgact ccagccagga ggtgaccttc ttcctgccca ctgagacggc    1800
ttttgacaag ttgtcggacg cgctgggcgt tgccaggagc aaccgtgcgg gtttgttgcc    1860
gtacttgccg gttatcaaaa gagccctaag ctatcacgtg ctaccgacca gaattagcct    1920
tcagagtgtt gcgaatcaat cagtcggcgg tacggagtac tacaacacca cgcttacgat    1980
gggacagtcc tcaagcatcg gcgtgcgggt ttcgcctccc tcgagccccc cggcgacatc    2040
cccggagata ttcattctgg gggttagctc aaccgctaaa gtactgcagg ctgatgtcgc    2100
ggcaggcgcg tcgtgcatta atgtcgtgga taccgttttg cagtattggt acaactcagt    2160
tgatgaggtc ttcgcctcca tcagcggcgc ctcgaccatg taccaggcgc tcaagaccgc    2220
ccaacttctc aagccagcga atgtgacgag cccgtacacc atattcgtac caaccgacga    2280
ggccttcgtc agcgccttcg gtgcctccgc cgctaccacc atcctcgcca atctaaggtc    2340
gtacgaaagc ttgctacgtc accatgtggc atacggctgg gtggttacgg acacaacctc    2400
agaagaatac gttcgtacat cgtacataac tctgaattcg aacaacgtga cggttgtggt    2460
tccatcgaac gacaaggccg atgctggcgt caagcccacc gtcgcctcag ctgccgtacc    2520
cggatcccca gtcttctcca tcctaaatac attccaagtc ggcatcgagc acaagtgat    2580 cgtccaagtg attaatgggg ttcttaaccc ggctagcagt cggcagacag ccggtggcgc    2640
agcgatggcc aagggcgagg agctgttcac cggtgtggtc cccatcctgg tggagctgga    2700
cggcgacgtg aacggccaca gttctccgt ctccggcgag ggtgagggtg acgccaccta    2760
cggcaagctg accctgaagt tcatctgcac caccggcaag ctgcccgtgc cctggcccac    2820
cctggtcacc accctgacct acggtgtgca gtgcttctcc cgctaccccg accacatgaa    2880
gcagcacgac ttcttcaagt ccgccatgcc cgagggctac gtgcaggagc gcaccatctt    2940
cttcaaggac gacggcaact acaagacccg cgccgaggtc aagttcgagg gcgacaccct    3000
ggtgaaccgc atcgagctga agggcatcga cttcaaggag gacggcaaca tcctgggcca    3060
caagctggag tacaactaca actcccacaa cgtgtacatc atggccgaca agcagaagaa    3120
cggcatcaag gtgaacttca gatccgcca caacatcgag gacggctccg tgcagctggc    3180
cgaccactac cagcagaaca ccccccatcgg cgatggcccc gtgctgctgc ccgacaacca    3240
ctacctgtcc atccagtccg ccctgtccaa ggaccccaac gagaagcgcg accacatggt    3300
cctgctggag ttcgtcaccg ctgccggcat cacccacggc atggacgagc tgtacaagta    3360
aggatccccg ctccgtgtaa atggaggcgc tcgttgatct gagccttgcc ccctgacgaa    3420
cggcggtgga tggaagatac tgctctcaag tgctgaagcg gtagcttagc tccccgtttc    3480
gtgctgatca gtctttttca acacgtaaaa agcggaggag ttttgcaatt ttgttggttg    3540
taacgatcct ccgttgattt tggcctcttt ctccatgggc gggctgggcg tatttgaagc    3600
gggtacccag cttttgttcc ctttagtgag ggttaattgc gcgcttggcg taatcatggt    3660
```

```
catagctgtt tcctgtgtga aattgttatc cgctcacaat tccacacaac atacgagccg   3720
gaagcataaa gtgtaaagcc tggggtgcct aatgagtgag ctaactcaca ttaattgcgt   3780
tgcgctcact gcccgctttc cagtcgggaa acctgtcgtg ccagctgcat taatgaatcg   3840
gccaacgcgc ggggagaggc ggtttgcgta ttgggcgctc ttccgcttcc tcgctcactg   3900
actcgctgcg ctcggtcgtt cggctgcggc gagcggtatc agctcactca aaggcggtaa   3960
tacggttatc cacagaatca ggggataacg caggaaagaa catgtgagca aaaggccagc   4020
aaaaggccag gaaccgtaaa aaggccgcgt tgctggcgtt tttccatagg ctccgccccc   4080
ctgacgagca tcacaaaaat cgacgctcaa gtcagaggtg gcgaaacccg acaggactat   4140
aaagatacca ggcgtttccc cctggaagct ccctcgtgcg ctctcctgtt ccgaccctgc   4200
cgcttaccgg atacctgtcc gcctttctcc cttcgggaag cgtggcgctt tctcatagct   4260
cacgctgtag gtatctcagt tcggtgtagg tcgttcgctc caagctgggc tgtgtgcacg   4320
aaccccccgt tcagcccgac cgctgcgcct tatccggtaa ctatcgtctt gagtccaacc   4380
cggtaagaca cgacttatcg ccactggcag cagccactgg taacaggatt agcagagcga   4440
ggtatgtagg cggtgctaca gagttcttga agtggtggcc taactacggc tacactagaa   4500
ggacagtatt tggtatctgc gctctgctga gccagttacc ttcggaaaaa gagttggta   4560 gctcttgatc cggcaaacaa accaccgctg gtagcggtgg ttttttttgtt tgcaagcagc   4620 agattacgcg cagaaaaaaa ggatctcaag aagatccttt gatcttttct acggggtctg   4680
acgctcagtg gaacgaaaac tcacgttaag ggattttggt catgagatta tcaaaaagga   4740
tcttcaccta gatcctttta aattaaaaat gaagttttaa atcaatctaa agtatatatg   4800
agtaaacttg gtctgacagt taccaatgct taatcagtga ggcacctatc tcagcgatct   4860
gtctatttcg ttcatccata gttgcctgac tccccgtcgt gtagataact acgatacggg   4920
agggcttacc atctggcccc agtgctgcaa tgataccgcg agaccacgc tcaccggctc   4980 cagatttatc agcaataaac cagccagccg gaagggccga gcgcagaagt ggtcctgcaa   5040
ctttatccgc ctccatccag tctattaatt gttgccggga agctagagta agtagttcgc   5100
cagttaatag tttgcgcaac gttgttgcca ttgctacagg catcgtggtg tcacgctcgt   5160
cgtttggtat ggcttcattc agctccggtt cccaacgatc aaggcgagtt acatgatccc   5220
ccatgttgtg caaaaaagcg gttagctcct tcggtcctcc gatcgttgtc agaagtaagt   5280
tggccgcagt gttatcactc atggttatgg cagcactgca taattctctt actgtcatgc   5340
catccgtaag atgcttttct gtgactggtg agtactcaac caagtcattc tgagaatagt   5400
gtatgcggcg accgagttgc tcttgcccgg cgtcaatacg ggataatacc gcgccacata   5460
gcagaacttt aaaagtgctc atcattggaa acgttcttc ggggcgaaaa ctctcaagga   5520
tcttaccgct gttgagatcc agttcgatgt aacccactcg tgcacccaac tgatcttcag   5580
catcttttac tttcaccagc gtttctgggt gagcaaaaac aggaaggcaa aatgccgcaa   5640
aaaagggaat aagggcgaca cggaaatgtt gaatactcat actcttcctt tttcaatatt   5700
attgaagcat ttatcagggt tattgtctca tgagcggata catatttgaa tgtatttaga   5760
aaaataaaca aataggggtt ccgcgcacat ttccccgaaa agtgccac              5808
```

<210> SEQ ID NO 15
<211> LENGTH: 23
<212> TYPE: DNA
<213> ORGANISM: V. carteri

<400> SEQUENCE: 15
atgcggatgg caatcgctgc ctt                                    23

<210> SEQ ID NO 16
<211> LENGTH: 19
<212> TYPE: DNA
<213> ORGANISM: V. carteri

<400> SEQUENCE: 16
tcacgctgcg ccaccggct                                         19

<210> SEQ ID NO 17
<211> LENGTH: 39
<212> TYPE: DNA
<213> ORGANISM: C. reinhardtii

<400> SEQUENCE: 17
acggctcgag ggaagatcta gccatggcca agggcgagg                   39

<210> SEQ ID NO 18
<211> LENGTH: 28
<212> TYPE: DNA
<213> ORGANISM: C. reinhardtii

<400> SEQUENCE: 18
acggggatcc ttacttgtac agctcgtc                               28

<210> SEQ ID NO 19
<211> LENGTH: 22
<212> TYPE: DNA
<213> ORGANISM: C. reinhardtii

<400> SEQUENCE: 19
agatctatgc ggatggcaat cg                                     22

<210> SEQ ID NO 20
<211> LENGTH: 22
<212> TYPE: DNA
<213> ORGANISM: C. reinhardtii

<400> SEQUENCE: 20
tggccatcgc tgcgccaccg gc                                     22

<210> SEQ ID NO 21
<211> LENGTH: 40
<212> TYPE: DNA
<213> ORGANISM: C. reinhardtii

<400> SEQUENCE: 21
tggccatgga ggagccggag gagcccgctg cgccaccggc                  40

<210> SEQ ID NO 22
<211> LENGTH: 19
<212> TYPE: DNA
<213> ORGANISM: V. carteri

<400> SEQUENCE: 22
aacgacaagg ccgatgctg                                         19

<210> SEQ ID NO 23
<211> LENGTH: 20
<212> TYPE: DNA
<213> ORGANISM: V. carteri

-continued

```
<400> SEQUENCE: 23
gcttgtggcc caggatgttg                                               20

<210> SEQ ID NO 24
<211> LENGTH: 19
<212> TYPE: DNA
<213> ORGANISM: V. carteri

<400> SEQUENCE: 24
aaatggccag gtgagtcga                                                19

<210> SEQ ID NO 25
<211> LENGTH: 20
<212> TYPE: DNA
<213> ORGANISM: V. carteri

<400> SEQUENCE: 25
gctggatgcg ggacttgttg                                               20

<210> SEQ ID NO 26
<211> LENGTH: 20
<212> TYPE: DNA
<213> ORGANISM: V. carteri

<400> SEQUENCE: 26
ggtatcgtgc tggactctgg                                               20

<210> SEQ ID NO 27
<211> LENGTH: 19
<212> TYPE: DNA
<213> ORGANISM: V. carteri

<400> SEQUENCE: 27
gggttaaaca gcacctcgg                                                19
```